United States Patent [19]

Kosaka et al.

[11] Patent Number: 5,695,684
[45] Date of Patent: Dec. 9, 1997

[54] MESOMORPHIC COMPOUND, LIQUID CRYSTAL COMPOSITION CONTAINING THE COMPOUND, LIQUID CRYSTAL DEVICE USING THE COMPOSITION, LIQUID CRYSTAL APPARATUS AND DISPLAY METHOD

[75] Inventors: Yoko Kosaka, Atsugi; Takao Takiguchi, Tokyo; Takashi Iwaki, Machida; Takeshi Togano, Yokohama; Shinichi Nakamura, Isehara, all of Japan

[73] Assignee: Canon Kabushiki Kaisha, Tokyo, Japan

[21] Appl. No.: 411,218

[22] Filed: Mar. 27, 1995

[30] Foreign Application Priority Data

Mar. 25, 1994 [JP] Japan .................... 6-077749

[51] Int. Cl.$^6$ ............... C09K 19/32; G02F 1/13; C07D 215/00
[52] U.S. Cl. ............... 252/299.62; 252/299.61; 252/299.63; 349/184; 546/152; 546/154; 546/167; 546/168; 546/172; 546/173; 546/174; 546/176; 546/177; 546/178; 546/180; 546/181; 546/183
[58] Field of Search ............... 252/299.61, 299.01, 252/299.62, 299.63; 546/154, 152, 167, 180, 183, 173, 181, 168, 172, 174, 176, 177, 178; 349/184

[56] References Cited

U.S. PATENT DOCUMENTS 5,462,694  10/1995  Kosaka et al. ............ 252/299.61

FOREIGN PATENT DOCUMENTS 0374849  6/1990  European Pat. Off. .

OTHER PUBLICATIONS

Leardini et al., Liquid Crystals, vol. 2, No. 5 (1987) pp. 625–631.

*Primary Examiner*—Shean C. Wu
*Attorney, Agent, or Firm*—Fitzpatrick, Cella, Harper & Scinto

[57] ABSTRACT

A mesomorphic compound represented by a formula (I) containing a quinoline-2,6-diyl skeleton is suitable as a component for a liquid crystal composition providing improved response characteristics and a high contrast. A liquid crystal device is constituted by disposing the liquid crystal composition between a pair of electrode plates. The liquid crystal device may preferably be used as a display panel constituting a liquid crystal apparatus providing good display characteristics.

25 Claims, 9 Drawing Sheets

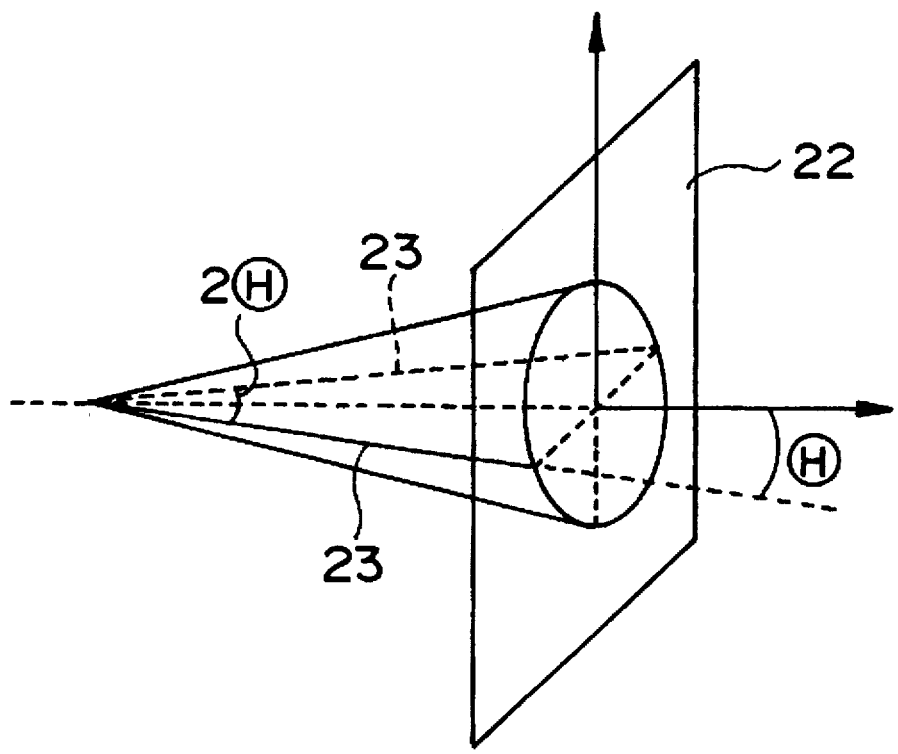
F I G. 4

MESOMORPHIC COMPOUND, LIQUID CRYSTAL COMPOSITION CONTAINING THE COMPOUND, LIQUID CRYSTAL DEVICE USING THE COMPOSITION, LIQUID CRYSTAL APPARATUS AND DISPLAY METHOD

FIELD OF THE INVENTION AND RELATED ART

The present invention relates to a mesomorphic compound, a liquid crystal composition, a liquid crystal device, a liquid crystal apparatus and a display method, and more particularly to an optically inactive mesomorphic compound, a liquid crystal composition containing the compound with improved responsiveness to an electric field, a liquid crystal device using the composition for use in a liquid crystal display device, a liquid crystal-optical shutter, etc., a liquid crystal apparatus using the device particularly as a display device, and a display method of using the composition.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. have been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, conventional ferroelectric liquid crystal materials do not sufficiently satisfy characteristics required for a liquid crystal device including low-temperature operation characteristic, high-speed responsiveness, high contrast, etc.

More specifically, among a response time $\tau$, the magnitude of spontaneous polarization Ps and viscosity $\eta$, the following relationship (II) exists: $\tau = \eta/(Ps \cdot E)$ ... (II), where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°–40° C., the response speed changes by a factor of about 20, so that it actually exceeds the range controllable by driving voltage and frequency.

In general, in a liquid crystal device utilizing birefringence of a liquid crystal, the transmittance under right angle cross nicols is given by the following equation:

$$I/I_0 = \sin^2 4\theta \cdot \sin^2(\Delta n d/\lambda)\pi,$$

wherein $I_0$: incident light intensity,

I: transmitted light intensity,

θ: tilt angle,

Δn: refractive index anisotropy, d: thickness of the liquid crystal layer,

λ: wavelength of the incident light.

Tilt angle θ in a ferroelectric liquid crystal with non-helical structure is recognized as a half of an angle between the average molecular axis directions of liquid crystal molecules in a twisted alignment in a first orientation state and a second orientation state. According to the above equation, it is shown that a tilt angle θ of 22.5 degrees provides a maximum transmittance and the tilt angle θ in a non-helical structure for realizing bistability should desirably be as close as possible to 22.5 degrees in order to provide a high transmittance and a high contrast.

However, when a birefringence of a liquid crystal is utilized in a liquid crystal device using a ferroelectric liquid crystal in a non-helical structure exhibiting bistability reported by Clark and Lagerwall, the following problems are encountered, thus leading to a decrease in contrast.

First, a tile angle θ in a ferroelectric liquid crystal with a non-helical structure obtained by alignment with a polyimide film treated by rubbing of the prior art has become smaller as compared with a tilt angle Ⓗ (the angle Ⓗ is a half of the apex angle of the cone shown in FIG. 4 as described below) in the ferroelectric liquid crystal having a helical structure, thus resulting in a lower transmittance.

Secondly, even if the device provides a high contrast in a static state, i.e., under no electric field application, liquid crystal molecules fluctuate due to a slight electric field at a non-selection period of time in a matrix drive scheme in the case of applying a voltage to the liquid crystal molecules for providing a display image, thus resulting in the display image including a light (or pale) black display state, i.e., a decrease in a contrast.

Thus, as described hereinabove, commercialization of a ferroelectric liquid crystal device requires a liquid crystal composition assuming a chiral smectic phase which provides a high contrast, a high-speed responsiveness and a small temperature-dependence of response speed.

In order to afford uniform switching characteristics at display, a good view-angle characteristic, a good storage stability at a low temperature, a decrease in a load to a driving IC (integrated circuit), etc. to the above-mentioned ferroelectric liquid crystal device or a display apparatus including the ferroelectric liquid crystal device; the above-mentioned liquid crystal composition is required to optimize its properties such as spontaneous polarization, a helical pitch in chiral smectic C (SmC*) phase, a helical pitch in cholesteric (Ch) phase, a temperature range showing a mesomorphic phase, optical anisotropy, a tilt angle and dielectric anisotropy.

SUMMARY OF THE INVENTION

An object of the present invention is to provide a mesomorphic compound providing a high speed responsiveness, a high contrast and a decreased temperature-dependence of response speed; a liquid crystal composition, particularly a chiral smectic liquid crystal composition containing the mesomorphic compound for providing a practical liquid crystal device including a ferroelectric liquid crystal device as described above; a liquid crystal device including the liquid crystal composition and affording good display performances; a liquid crystal apparatus including the device; and a display method using the composition.

According to the present invention, there is provided a mesomorphic compound represented by the following formula (I):

wherein

Q is quinoline-2,6-diyl;

$A_1$ denotes —$A_2$—$R_2$ or —$A_3$—$R_3$ in which $A_2$ denotes 1,4-phenylene capable of having one or two substituents selected from F, Cl, $CH_3$, $CF_3$ and CN; thiophene-2,5-diyl; indan-2,5-diyl; 2-alkylindan-2,5-diyl having a linear or branched alkyl group having 1–18 carbon atoms; coumaran-2,5-diyl; 2-alkylcoumaran-2,5-diyl having a linear or branched alkyl group having 1–18 carbon atoms; benzofuran-2,5-diyl; or benzofuran-2,6-diyl;

$A_3$ denotes pyrimidine-2,5-diyl; pyridine-2,5-diyl; pyrazine-2,5-diyl; pyridazine-3,6-diyl; 1,4-cyclohexylene; 2,6-naphthylene; quinoxaline-2,6-diyl; or quinoline-2,6-diyl;

$R_1$ and $R_3$ independently denote F; CN; $CF_3$; or a linear, branched or cyclized alkyl group having 1–20 carbon atoms capable of including at least one —$CH_2$— group which can be replaced with —O—, —S—, —CO—, —*$CY_1(Y_2)$—, —CH=CH— or —C≡C— provided that heteroatoms are not adjacent to each other and capable of including at least one —$CH_3$ group which can be replaced with —$CH_2F$, —$CHF_2$ or —CN; in which $Y_1$ and $Y_2$ independently denote H, F, $CH_2F$, $CHF_2$, $CF_3$, CN or a linear alkyl group having 1–5 carbon atoms; and *C denotes an asymmetric carbon atom; and $R_2$ denotes F; CN; $CF_3$; or a linear, branched or cyclized alkyl group having 1–20 carbon atoms capable of including at least one —$CH_2$— group which can be replaced with —*$CY_1(Y_2)$—, —CH=CH— or —C≡C— and capable of including at least one —$CH_3$ group which can be replaced with —$CH_2F$, —$CHF_2$ or —CN; in which $Y_1$, $Y_2$ and *C have the same meanings as defined above.

According to the present invention, there is further provided a liquid crystal composition containing at least one species of the above-mentioned mesomorphic compound.

The present invention provides a liquid crystal device comprising a pair of electrode plates and the liquid crystal composition described above disposed between the electrode plates.

The present invention further provides a liquid crystal apparatus including the liquid crystal device, particularly including a display panel comprising the liquid crystal device.

The present invention still further provides a display method of using the liquid crystal composition described above and controlling the alignment direction of liquid crystal molecules in accordance with image data to effect display.

Heretofore, there have been known mesomorphic compounds having a quinoline-2,6-diyl group as disclosed in Japanese Laid-Open Patent Applications (JP-A) (Kokai) Nos. 4-316555 and 4-368370.

These compounds have an either or ester linkage between a terminal alkyl group and an inner 1,4-phenylene skeleton. Thus, these compounds are distinguished from the above-mentioned mesomorphic compound of the formula (I) capable of containing a 1,4-phenylene skeleton directly connected to a terminal alkyl group.

As will be apparent from the results of Example 14 and Comparative Example 4 (appearing hereinbelow), a mesomorphic compound of the formula (I) according to the present invention provides improved responsive characteristics over a mesomorphic compound having an ether linkage between a terminal alkyl group and an inner 1,4-phenylene skeleton.

We have found that a mesomorphic compound represented by the formula (I) is suitable as a component of a liquid crystal composition, particularly a chiral smectic liquid crystal composition, and a liquid crystal device including the liquid crystal composition which provide good display characteristics based on improvements in various characteristics such as an alignment characteristic, switching characteristic, responsiveness, a temperature-dependence of response speed, and a contrast. As the mesomorphic compound of the formula (I) according to the present invention has a good compatibility with another (mesomorphic) compound used herein, it is possible to use the mesomorphic compound of the formula (I) for controlling various properties such as spontaneous polarization, SmC* pitch, Ch pitch, a temperature range showing a mesomorphic phase, optical anisotropy, a tilt angle and dielectric anisotropy, with respect to a liquid crystal mixture or composition.

These and other objects, features and advantages of the present invention will become more apparent upon a consideration of the following description of the preferred embodiments of the present invention taken in conjunction with the acympanying drawings.

BRIEF DESCRIPTION OF THE DRAWINGS

FIG. 4 is a schematic view for illustrating a tilt angle (H) in a ferroelectric liquid crystal with a helical structure.

DETAILED DESCRIPTION OF THE INVENTION

Figure 1:
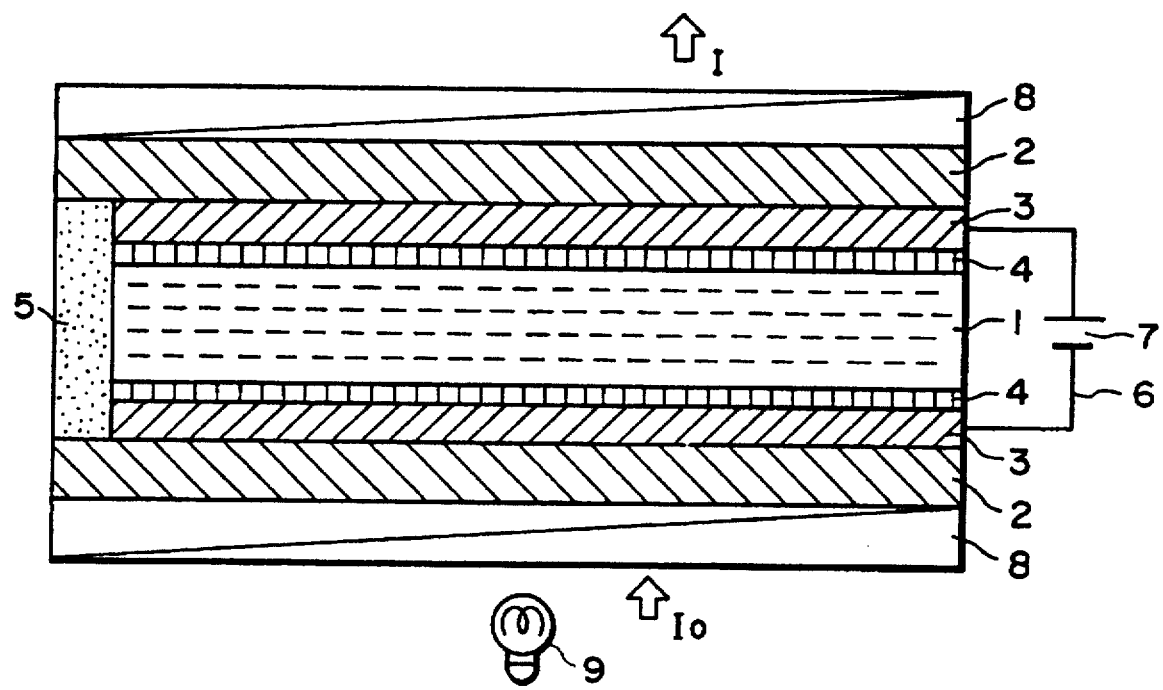
FIG. 1 is a schematic sectional view of a liquid crystal device using a liquid crystal composition assuming a chiral smectic phase.

The mesomorphic compound of the formula (I) according to the present invention is characterized by containing a quinoline-2,6-diyl skeleton between $R_1$ and $A_1$ described above. The mesomorphic compound of the formula (I) may be

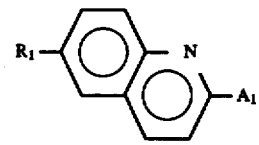

or

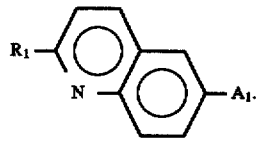

In view of improvements in various properties including: a temperature range of a mesomorphic phase, response characteristics when contained in liquid crystal composition, viscosity, and alignment characteristic; the mesomorphic compound of the formula (I) may preferably satisfy at least one of the following conditions (a)–(c):

(a) $R_1$ is any one of the groups (1)–(5) shown below,
(b) $R_2$ is any one of the groups (6)–(10) shown below, and
(c) $R_3$ is any one of the groups (1)–(5) shown below,

 (1)

 (2)

 (3)

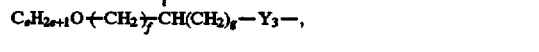 (4)

and

 (5)

and

 (6)

 (7)

 (8)

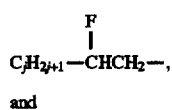

(9)

and

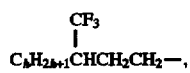

(10)

wherein a is an integer of 1–16; d and g independently denotes an integer of 0–7; b, e, h and j independently denotes an integer of 1–10; f is 0 or 1, with the proviso that b+d≦16 and e+f+g≦16; $Y_3$ is a sigle bond, —O—, —OCO— or —COO—; and $Y_4$ is —CH$_2$O—, —CH$_2$— or —COO—.

in which the cyclized structure can be constituted by methylene group (or hydrocarbon group) and/or at least one heteroatom (e.g., oxygen) and at least one methylene group (or hydrocarbon group) in the alkyl group can be replaced with —O— or —CO—.

Herein, the term "mesomorphic compound" covers not only a compound assuming a mesomorphic (liquid crystal) phase but also a compound not assuming a mesomorphic phase per se as long as a liquid crystal composition containing such a compound assumes a mesomorphic phase.

The mesomorphic compound of the formula (I) may generally be synthesized through, e.g., the following reaction schemes.

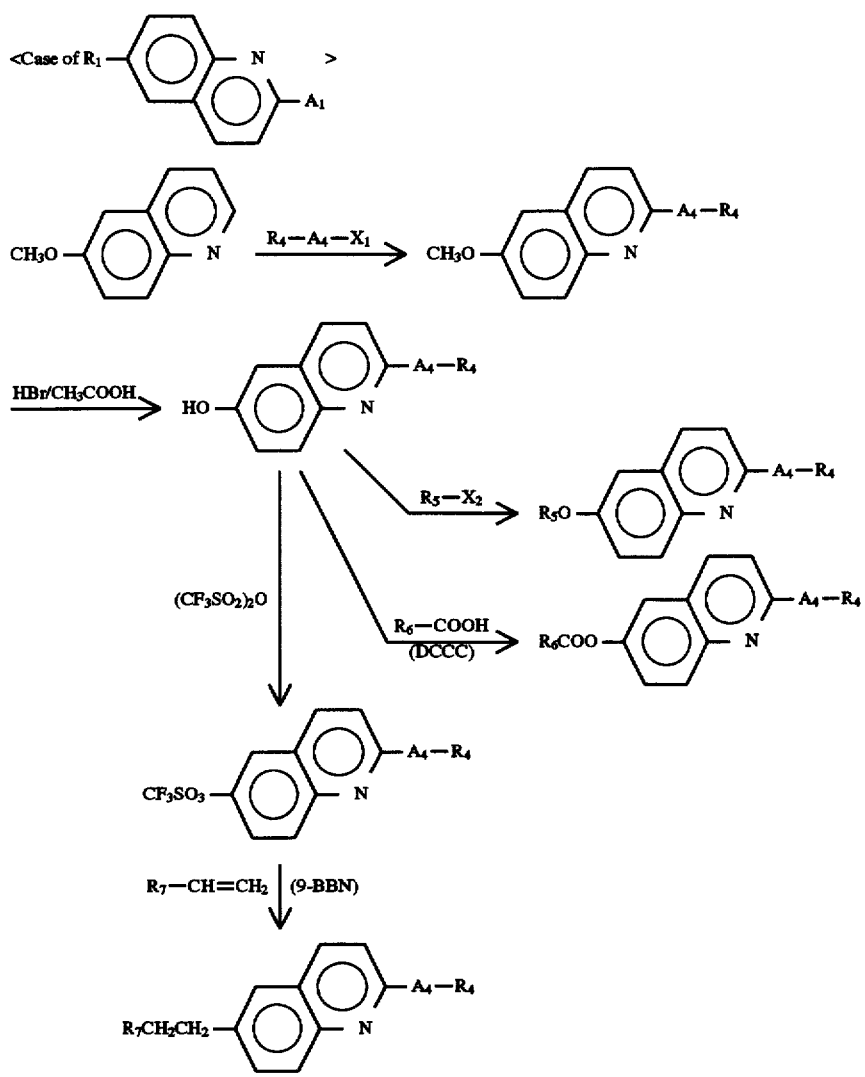

The above groups may be optically active group or optically inactive group, preferably be optically inactive group.

In the above-mentioned formula (I), $A_1$ may preferably be —$A_2$—$R_2$ and $A_2$ may preferably be 1,4-phenylene. Further, $R_1$ may preferably be the above-mentioned group (1) and $R_2$ may preferably be the above-mentioned group (6).

$R_1$, $R_2$ and $R_3$ may be a cyclized alkyl group as described above. Herein, "cyclized alkyl group" means a cyclic alkyl group or an alkyl group having a partially cyclized structure In the above reaction scheme, —$A_4$—$R_4$ is —$A_2$—$R_2$ or —$A_3$—$R_3$ wherein $A_2$, $A_3$, $R_2$ and $R_3$ have the same meanings as defined above. $R_5$ is a linear, branched or cyclized alkyl group having 1–19 carbon atoms, and $R_6$ and $R_7$ independently denote a linear, branched or cyclized alkyl group having 1–18 carbon atoms. In the alkyl group of $R_5$, $R_6$ or $R_7$; one or two or more —CH$_2$— groups can be replaced by —O—, —S—, —CO—, —*C$Y_1$($Y_1$)—, —CH=CH— or —C≡C— on condition that heteroatoms are not adjacent to each other wherein $Y_1$ end $Y_2$ have the same meanings as described above. In the alkyl group of $R_5$, $R_6$ or $R_7$; one or two or more —$CH_3$ groups can be replaced by —$CH_2F$, —$CHF_2$ or —CN. $X_1$ is halogen atom such as iodine or bromine, and $X_2$ is p-toluenesulfonyl(tosyl) group or halogen atom such as iodine or bromine. "DCC" means 1,3-dicyclohexylcarbodiimide and "9-BBN" means 9-borabicyclo[3.3.1]-nonane.

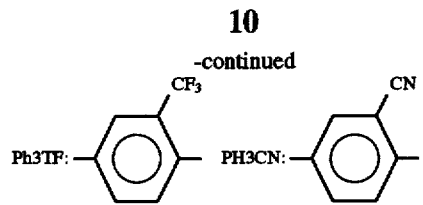

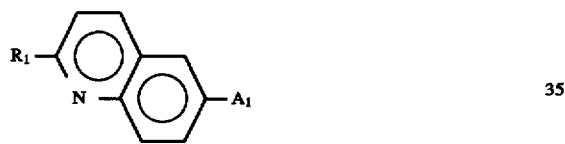

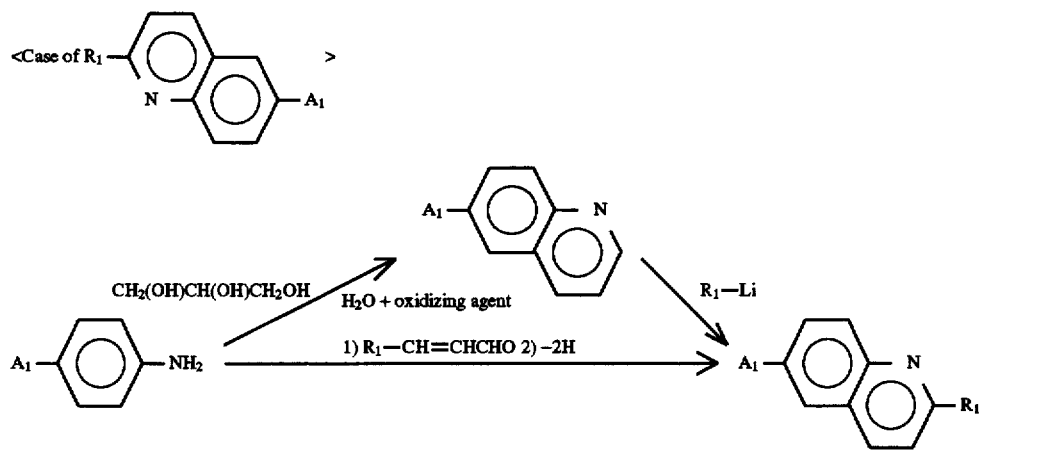

In the above, $A_1$ and $R_1$ are the same as those defined above. It is possible to synthesize

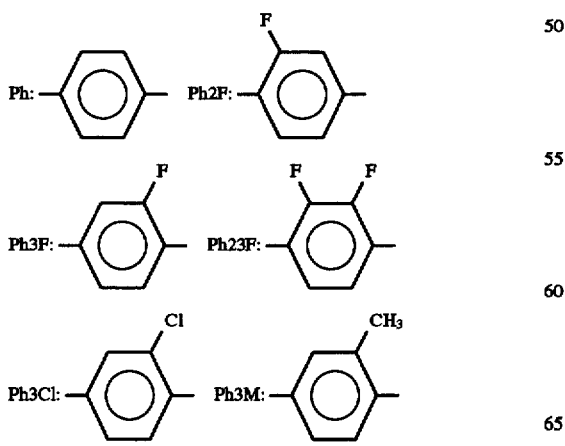

by using a group, capable of being modified into $A_1$, at 4-position of aniline and deriving $A_1$ from the above group after ring closure (formation of quinoline ring).

Specific examples of the (optically active or inactive) mesomorphic compound of the formula (I) may include those represented by the following structural formulae including abbreviations used herein for respective cyclic groups listed below.

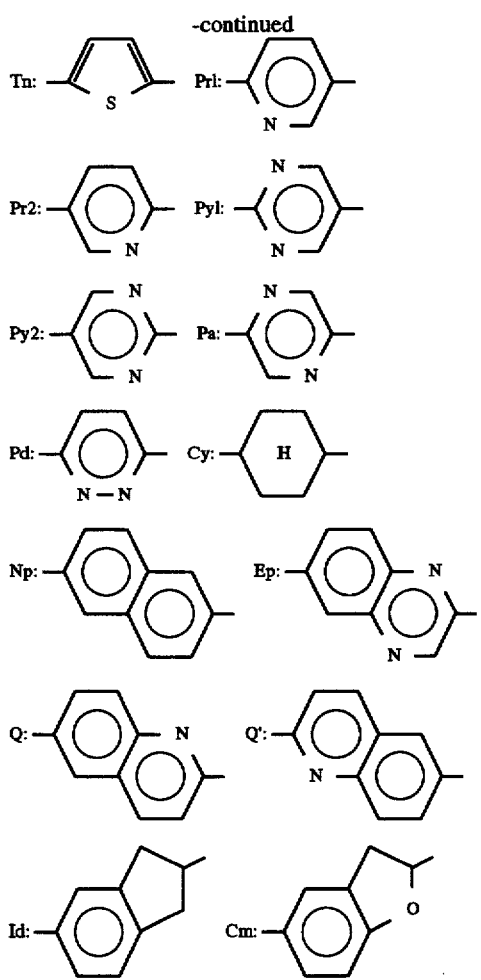

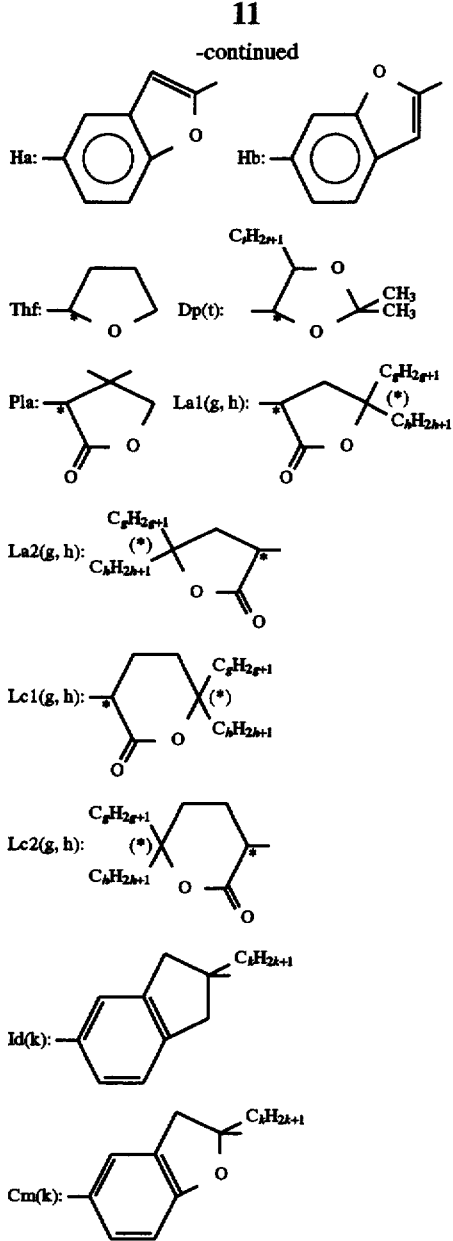

In the above, g, h and t is an integer of 0–10 and k is an integer of 1–18.

(I-1) $C_4H_9$-Q-Ph-$C_5H_{11}$
(I-2) $C_7H_{15}$-Q-Ph-$C_3H_7$
(I-3) $C_{10}H_{21}$-Q-Ph-$C_5H_{11}$
(I-4) $C_{11}H_{23}$-Q-Ph-$C_8H_{17}$
(I-5) $C_{14}H_{29}$-Q-Ph-$C_6H_{13}$
(I-6) $CH_3O$-Q-Ph-$C_5H_{11}$
(I-7) $C_4H_9O$-Q-Ph-$C_{10}H_{21}$
(I-8) $C_5H_{11}O$-Q-Ph-$C_{11}H_{23}$
(I-9) $C_9H_{19}O$-Q-Ph-$C_8H_{17}$
(I-10) $C_{10}H_{21}O$-Q-Ph-$C_5H_{11}$
(I-11) $C_{12}H_{25}O$-Q-Ph-$C_9H_{19}$
(I-12) $C_{16}H_{33}$-Q-Ph-$CH_3$
(I-13) $C_6H_{13}COO$-Q-Ph-$C_{10}H_{21}$
(I-14) $C_8H_{17}COO$-Q-Ph-$C_5H_{11}$
(I-15) $C_{13}H_{27}COO$-Q-Ph-$C_2H_5$
(I-16) $C_2H_5COO$-Q-Ph-$C_{12}H_{25}$
(I-17) $CH_2=CH(CH_2)_6O$-Q-Ph-$C_4H_9$
(I-18) $C_8H_{17}$*CH(F)$CH_2O$-Q-Ph-$C_7H_{15}$
(I-19) $C_3H_7$*CH(CF$_3$)(CH$_2$)$_2$O-Q-Ph-$C_3H_7$
(I-20) $C_2H_5$*CH(CH$_3$)CH$_2$O-Q-Ph-$C_8H_{17}$
(I-21) $C_2H_5OCH(CH_3)CH_2O$-Q-Ph-$C_6H_{13}$
(I-22) $C_6H_{13}$*CH(F)COO-Q-Ph-$C_{10}H_{21}$
(I-23) $C_4H_9$*CH(CF$_3$)COO-Q-Ph-$C_5H_{11}$
(I-24) $C_6H_{13}$-Q-Tn-$C_6H_{13}$
(I-25) $C_9H_{19}$-Q-Tn-$C_5H_{11}$
(I-26) $C_3H_7O$-Q-Tn-$C_7H_{15}$
(I-27) $C_7H_{15}O$-Q-Tn-$C_9H_{19}$
(I-28) $C_5H_{11}COO$-Q-Tn-$C_4H_9$
(I-29) $C_{11}H_{23}COO$-Q-Tn-$C_8H_{17}$
(I-30) $C_5H_{11}$-Q-Id-$C_{10}H_{21}$
(I-31) $C_8H_{17}$-Q-Id-$C_8H_{17}$
(I-32) $C_6H_{13}O$-Q-Id-$C_7H_{15}$
(I-33) $C_{10}H_{21}O$-Q-Id-$C_2H_5$
(I-34) $C_4H_9COO$-Q-Id-$C_6H_{13}$
(I-35) $C_8H_{17}$-Q-Cm-$C_8H_{17}$
(I-36) $C_{12}H_{25}$-Q-Cm-$C_{10}H_{21}$
(I-37) $C_5H_{11}O$-Q-Cm-$C_9H_{19}$
(I-38) $C_7H_{15}COO$-Q-Cm-$C_{12}H_{25}$
(I-39) $C_4H_9$-Q-Ha-$C_6H_{13}$
(I-40) $C_{10}H_{21}$-Q-Ha-$C_{11}H_{23}$
(I-41) $C_8H_{17}O$-Q-Ha-$C_{10}H_{21}$
(I-42) $C_6H_{13}COO$-Q-Ha-$C_5H_{11}$
(I-43) $C_6H_{13}$-Q-Hb-$C_8H_{17}$
(I-44) $C_{12}H_{25}$-Q-Hb-$C_4H_9$
(I-45) $C_2H_5O$-Q-Hb-$C_8H_{17}$
(I-46) $C_9H_{19}COO$-Q-Hb-$C_6H_{13}$
(I-47) $C_7H_{15}$*CH(F)COO-Q-Py1-$C_8H_{17}$
(I-48) $C_3H_7$-Q-Py1-$C_{10}H_{21}$
(I-49) $C_6H_{13}$-Q-Py1-$C_6H_{13}$
(I-50) $C_8H_{17}O$-Q-Py1-$C_9H_{19}$
(I-51) $C_9H_{19}O$-Q-Py1-$C_{11}H_{23}$
(I-52) $C_{10}H_{21}$-Q-Py1-$OC_9H_{19}$
(I-53) $C_6H_{13}$-Q-Py1-$OC_{11}H_{23}$
(I-54) $C_5H_{11}O$-Q-Py1-$OC_7H_{15}$
(I-55) $C_8H_{17}$-Q-Pr1-$C_4H_9$
(I-56) $C_{11}H_{23}O$-Q-Pr1-$C_6H_{13}$
(I-57) $C_7H_{15}$-Q-Pr1-$OC_6H_{13}$
(I-58) $C_6H_{13}$-Q-Pr2-$C_9H_{19}$
(I-59) $C_{10}H_{21}$-Q-Pr2-$C_4H_9$
(I-60) $C_3H_7O$-Q-Pr2-$C_8H_{17}$
(I-61) $C_5H_{11}$-Q-Cy-$C_6H_{13}$
(I-62) $C_{12}H_{25}O$-Q-Cy-$C_3H_7$
(I-63) $C_9H_{19}$-Q-Np-$C_{10}H_{21}$
(I-64) $C_8H_{17}$-Q-Np-$OC_6H_{13}$
(I-65) $C_{10}H_{21}$-Q-EP-$C_8H_{17}$
(I-66) $C_6H_{13}O$-Q-EP-$C_{10}H_{21}$
(I-67) $C_{11}H_{23}$-Q-Q-$C_5H_{11}$
(I-68) $CH_3O$-Q-Q-$C_{12}H_{25}$
(I-69) $C_4H_9$-Q-Ph2F-$C_{10}H_{21}$
(I-70) $C_{11}H_{23}O$-Q-Ph2F-$C_{11}H_{23}$
(I-71) $C_9H_{19}$-Q-Ph3F-$C_5H_{11}$
(I-72) $C_{10}H_{21}O$-Q-Ph3F-$C_9H_{19}$
(I-73) $C_6H_{13}O$-Q-Ph23F-$C_3H_7$
(I-74) $C_8H_{17}O$-Q-Ph3TF-$C_6H_{13}$
(I-75) $C_{12}H_{25}O$-Q-Ph3Cl-$C_4H_9$
(I-76) $C_9H_{19}O$-Q-Ph3M-$C_{10}H_{21}$
(I-77) $C_6H_{13}O$-Q-Ph3CN-$C_{12}H_{25}$
(I-78) $C_7H_{15}O$-Q-Ph-$CH_2CH(CH_3)CH_3$
(I-79) $C_6H_{13}$-Q-Py2-$CH_2$*CH(F)$C_6H_{13}$
(I-80) $C_8H_{17}$-Q-Np-$OCOCH_2$*CH(CF$_3$)$C_8H_{17}$
(I-81) $C_{12}H_{25}$-Q-Pa-$C_{10}H_{21}$
(I-82) $C_{12}H_{25}$-Q-Pd-$C_5H_{11}$
(I-83) $C_4H_9$*C(CN)(CH$_3$)COO-Q-Ph3F-$C_{10}H_{21}$
(I-84) $C_{10}H_{21}$-Q-Ph-F
(I-85) $C_{12}H_{25}O$-Q-Ph3F-F
(I-86) $C_9H_{19}$-Q-Ph-$CF_3$
(I-87) $C_8H_{17}O$-Q-Ph-CN (I-88) $C_9H_{19}O$-Q-Ph-F
(I-89) $CF_3$-Q-Ph-$C_5H_{11}$
(I-90) F-Q-Ph-$C_{10}H_{21}$
(I-91) $C_2H_5CH(CH_3)(CH_2)_3$-Q-Ph-$C_6H_{13}$
(I-92) $C_4H_9$-Q-Py2-$C_6H_{13}$
(I-93) $C_9H_{19}$-Q-Py2-$C_8H_{17}$
(I-94) $C_4H_9$-Q'-Ph-$C_5H_{11}$
(I-95) $C_7H_{15}$-Q'-Ph-$C_3H_7$
(I-96) $C_{10}H_{21}$-Q'-Ph-$C_5H_{11}$
(I-97) $C_{11}H_{23}$-Q'-Ph-$C_8H_{17}$
(I-98) $C_{14}H_{29}$-Q'-Ph-$C_6H_{13}$
(I-99) $C_{16}H_{33}$-Q'-Ph-$CH_3$
(I-100) $C_6H_{13}$-Q'-Tn-$C_6H_{13}$
(I-101) $C_9H_{19}$-Q'-Tn-$C_5H_{11}$
(I-102) $C_5H_{11}$-Q'-Id-$C_{10}H_{21}$
(I-103) $C_8H_{17}$-Q'-Id-$C_8H_{17}$
(I-104) $C_{12}H_{25}$-Q'-Cm-$C_{10}H_{21}$
(I-105) $C_8H_{17}$-Q'-Cm-$C_8H_{17}$
(I-106) $C_4H_9$-Q'-Ha-$C_6H_{13}$
(I-107) $C_{10}H_{21}$-Q'-Ha-$C_{11}H_{23}$
(I-108) $C_6H_{13}$-Q'-Hb-$C_8H_{17}$
(I-109) $C_{12}H_{25}$-Q'-Hb-$C_4H_9$
(I-110) $C_3H_7$-Q'-Py1-$C_{10}H_{21}$
(I-111) $C_6H_{13}$-Q'-Py1-$C_6H_{13}$
(I-112) $C_{10}H_{21}$-Q'-Py1-$OC_9H_{19}$
(I-113) $C_6H_{13}$-Q'-Py1-$OC_{11}H_{23}$
(I-114) $C_8H_{17}$-Q'-Pr1-$C_4H_9$
(I-115) $C_7H_{15}$-Q'-Pr1-$OC_6H_{13}$
(I-116) $C_5H_{11}$-Q'-Cy-$C_6H_{13}$
(I-117) $C_9H_{19}$-Q'-Np-$C_{10}H_{21}$
(I-118) $C_8H_{17}$-Q'-Np-$OC_6H_{13}$
(I-119) $C_4H_9$-Q'-Ph3F-$C_{10}H_{21}$
(I-120) $C_9H_{19}$-Q'-Ph3F-$C_5H_{11}$
(I-121) $C_8H_{17}$-Q'-Np-$OCOCH_2$*$CH(CF_3)C_8H_{17}$
(I-122) $C_{12}H_{25}$-Q'-Pa-$C_{10}H_{21}$
(I-123) $C_{12}H_{25}$-Q'-Pd-$C_5H_{11}$
(I-124) $C_{10}H_{21}$-Q'-Ph-F
(I-125) $C_9H_{19}$-Q'-Ph-$CF_3$
(I-126) $C_2H_5CH(CH_3)(CH_2)_3$-Q'-Ph-$C_6H_{13}$
(I-127) $C_{11}H_{23}$-Q-Id(8)-$C_8H_{17}$
(I-128) $C_{17}H_{35}$-Q-Ph-$C_5H_{11}$
(I-129) $C_{19}H_{39}$-Q-Cy-$CH_3$
(I-130) CN-Q-Np-$OC_6H_{13}$
(I-131) Lc1(8,0)-CHO-Q'-Ph-$C_8H_{17}$
(I-132) La1(1,1)-OCO-Q'-Id-$C_{10}H_{21}$
(I-133) Pla-COO-Q'-Ph-$C_{10}H_{21}$
(I-134) $C_{10}H_{21}$-Q-Cm(1)-$C_5H_{11}$
(I-135) $C_{18}H_{37}$-Q'-Tn-$C_3H_7$
(I-136) $C_{20}H_{41}$-Q-Ph2F-F
(I-137) Thf-COO-Q-Ph-$C_9H_{19}$
(I-138) $C_6H_{13}$-Q-Py1-OCH-Lc2(5,5)
(I-139) La2(6,0)-Q-Ph-$C_6H_{13}$
(I-140) $C_8H_{17}$-Q'-Np-O-Dp(2)

The liquid crystal composition according to the present invention may be obtained by mixing at least one species of the mesomorphic compound represented by the formula (I) and at least one species, preferably 1–50 species, more preferably 1–30 species, particularly 3–30 species, of another mesomorphic compound.

The liquid crystal composition according to the present invention may preferably be formulated as a liquid crystal composition capable of showing ferroelectricity, particularly a liquid crystal composition showing a chiral smectic phase and containing at least one optically active compound.

Specific examples of another mesomorphic compound described above may include those described at pages 23–39 of (JP-A) 4-272989 as compounds represented by formulae (III) to (XII), preferably formulae (IIIa) to (XIId), more preferably (IIIaa) to (IXIIdb).

In the above mesomorphic compounds of the formulae (III) to (XII), (IIIa) to (XIId) and (IIIaa) to (XIIdb), at least one terminal group (i.e., $R_1$' and/or $R_2$', $R_3$' and/or $R_4$', or $R_5$' and/or $R_6$') may be the group: $(CH_2)_EC_GF_{2G+1}$ in which E is an integer of 0–10 and G is an integer of 1–15.

In the present invention, mesomorphic compounds represented by the following formulae (XIII) to (XVIII) may also be used as another mesomorphic compound.

Specific examples of another mesomorphic compound may also include those represented by the following formulae (XIII) to (XVIII) including abbreviations for respective cyclic groups listed below in addition to those described above.

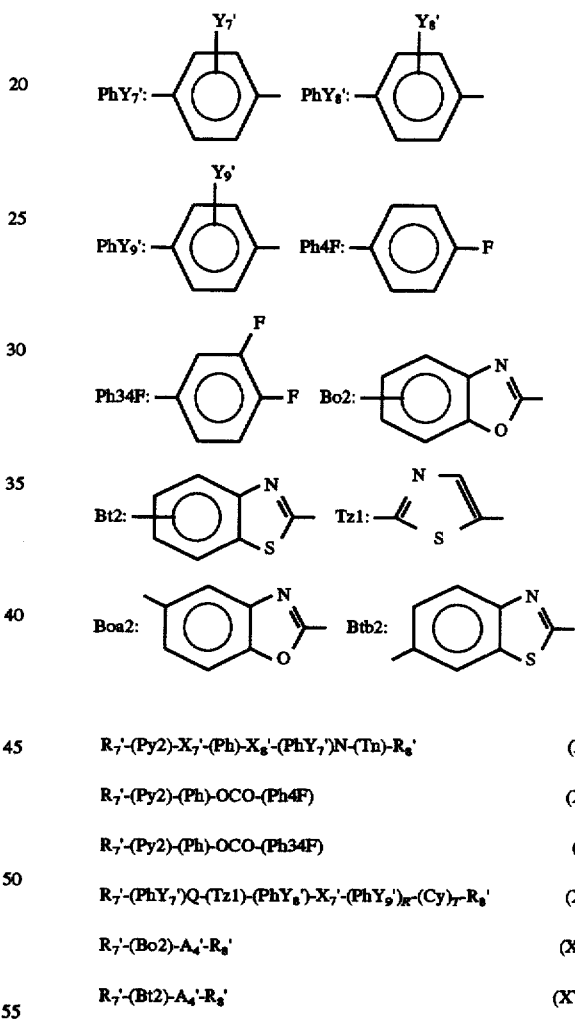

| | |
|---|---|
| $R_7$'-(Py2)-$X_7$'-(Ph)-$X_8$'-(PhY$_7$')N-(Tn)-$R_8$' | (XIII) |
| $R_7$'-(Py2)-(Ph)-OCO-(Ph4F) | (XIV) |
| $R_7$'-(Py2)-(Ph)-OCO-(Ph34F) | (XV) |
| $R_7$'-(PhY$_7$')Q-(Tz1)-(PhY$_8$')-$X_7$'-(PhY$_9$')$_K$-(Cy)$_T$-$R_8$' | (XVI) |
| $R_7$'-(Bo2)-$A_4$'-$R_8$' | (XVII) |
| $R_7$'-(Bt2)-$A_4$'-$R_8$' | (XVIII) |

Herein, $R_7$' and $R_8$' respectively denote hydrogen or a linear or branched alkyl group having 1– 18 carbon atoms capable of including one or non-neighboring two or more methylene groups which can be replaced with —O—, —CO—, —CH(CN)— or —CCH$_3$(CN)— provided that heteroatoms are not adjacent to each other and capable of including at least one H which can be replaced with F.

Further, preferred examples of $R_7$' and $R_8$' may respectively include those represented by the following groups (i) to (vii):

i) a linear alkyl group having 1–15 carbon atoms;

ii)

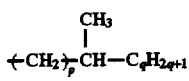

wherein p denotes an integer of 0–5 and q denotes an integer of 2–11 (optically active or inactive);

iii)

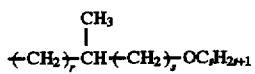

wherein r denotes an integer of 0–6, s denotes 0 or 1, and t denotes an integer of 1–14 (optically active or inactive);

iv)

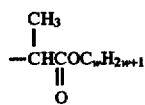

wherein w denotes an integer of 1–15 (optically active or inactive);

v)

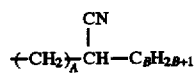

wherein A denotes an integer of 0–2 and B denotes an integer of 1–15 (optically active or inactive);

vi)

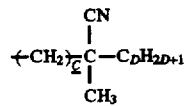

wherein C denotes an integer of 0–2 and D denotes an integer of 1–15 (optically active or inactive); and vii) H (hydrogen).

In the above formulae (XIII) to (XVIII); N, Q, R and T are 0 or 1; $Y_7'$, $Y_8'$ and $Y_9'$ are H or F; $A_4'$ is Ph or Np; and $X_7'$ and $X_8'$ respectively denote a single bond, —COO—, —OCO—, —CH$_2$O— or —OCH$_2$—.

The compound of the formula (XIII) may preferably include a compound represented by the following formula (XIIIa):

   (XIIIa).

The compound of the formula (XVI) may preferably include compounds represented by the following formulae (XVIa) and (XVIb):

   (XVIa), and

   (XVIb).

The compound of the formula (XVII) may preferably include compounds represented by the following formulae (XVIIa) and (XVIIb):

   (XVIIa), and $R_7'$-(Boa2)-(Np)-O-$R_8'$   (XVIIb).

The compounds of the formula (XVIII) and may preferably include compounds represented by the following formulae (XVIIIa) to (XVIIIc):

$R_7'$-(Btb2)-(Ph)-$R_8'$   (XVIIIa), $R_7'$-(Btb2)-(Ph)-O-$R_8'$   (XVIIIb), and $R_7'$-(Btb2)-(Np)-O-$R_8'$   (XVIIIc).

The compounds of the formula (XVIa) and (XVIb) may preferably include compounds represented by the following formulae (XVIaa) to (XVIbc):

$R_7'$-(Tz1)-(Ph)-O-$R_8'$   (XVIaa), $R_7'$-(Ph)-(Tz1)-(Ph)-$R_8'$   (XVIba), $R_7'$-(Ph)-(Tz1)-(Ph)-O-$R_8'$   (XVIbb), and $R_7'$-(Ph)-(Tz1)-(Ph)-OCO-$R_8'$   (XVIbc).

In formulating the liquid crystal composition according to the present invention by using at least one species of the mesomorphic compound of the formula (I), the liquid crystal composition may desirably contain 1–80 wt. % of a mesomorphic compound represented by the formula (I) (optically active or inactive) in view of improvements in various properties including a temperature range of a mesomorphic phase, responsiveness, contrast and switching characteristics so as to provide a practical liquid crystal device, particularly a (ferroelectric) chiral smectic liquid crystal device. Further, in view of properties of another mesomorphic compound in addition to the above properties, the liquid crystal composition according to the present invention may more preferably contain 1–60 wt. %, particularly 1–40 wt. %, of a mesomorphic compound of the formula (I). If the content of the mesomorphic compound of the formula (I) is below 1 wt. %, improvement effects (e.g., response characteristics) given by the mesomorphic compound of the formula (I) become too small in many cases. On the other hand, if the content of the mesomorphic compound of the formula (I) is in excess of 80 wt. %, a resultant liquid crystal composition is liable to cause precipitation at low temperature.

Similarly, when two or more species of the mesomorphic compounds represented by the formula (I) are used, the liquid crystal composition may desirably contain 1–80 wt. %, preferably 1–60 wt. %, more preferably 1–40 wt. %, of the two or more species of the mesomorphic compounds represented by the formula (I) (optically active or inactive) in view of the above-mentioned properties and effects.

The liquid crystal device according to the present invention may preferably be prepared by heating the liquid crystal composition as prepared above into an isotropic liquid under vacuum, filling a blank cell comprising a pair of oppositely spaced electrode plates with the composition, gradually cooling the cell to form a (chiral smectic) liquid crystal layer and restoring the normal pressure.

FIG. 1 is a schematic sectional view of an embodiment of the liquid crystal device, particularly utilizing ferroelectricity, as prepared above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. In the present invention, the transparent electrode 3 may be formed on one of the substrates 2. The glass substrates 2 are placed or arranged opposite each other. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to uniaxially align the liquid crystal molecules in the rubbing direction (uniaxial alignment treatment). Further, it is also possible to compose the alignment control layer 4 of two layers, e.g., by first forming an insulating layer of an inorganic material, such as silicon nitride, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyesterimide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer comprising the above-mentioned inorganic material or organic insulating alignment control layer comprising the above-mentioned organic material. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer 4 may have a thickness of ordinarily 1 nm–1 micron, preferably 1 nm–300 nm, further preferably 1 nm–100 nm. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, a sealing material comprising, e.g., an epoxy adhesive. Alternatively, a polymer film or glass fiber may also be used as a spacer. Between the two glass plates, a liquid crystal composition assuming a chiral smectic phase is sealed up to provide a liquid crystal layer 1 in a thickness of generally 0.5 to 20 μ, preferably 1 to 5 μm.

The transparent electrodes 3 are connected to the external power supply 7 through the lead wires 6. Further, outside the glass substrates 2, a pair of polarizers 8 arranged in, e.g., right angle cross nicol relationship are applied. The device shown in FIG. 1 is of a transmission type and accordingly is provided with a light source 9 at the back of one of the polarizers 8.

Figure 2:
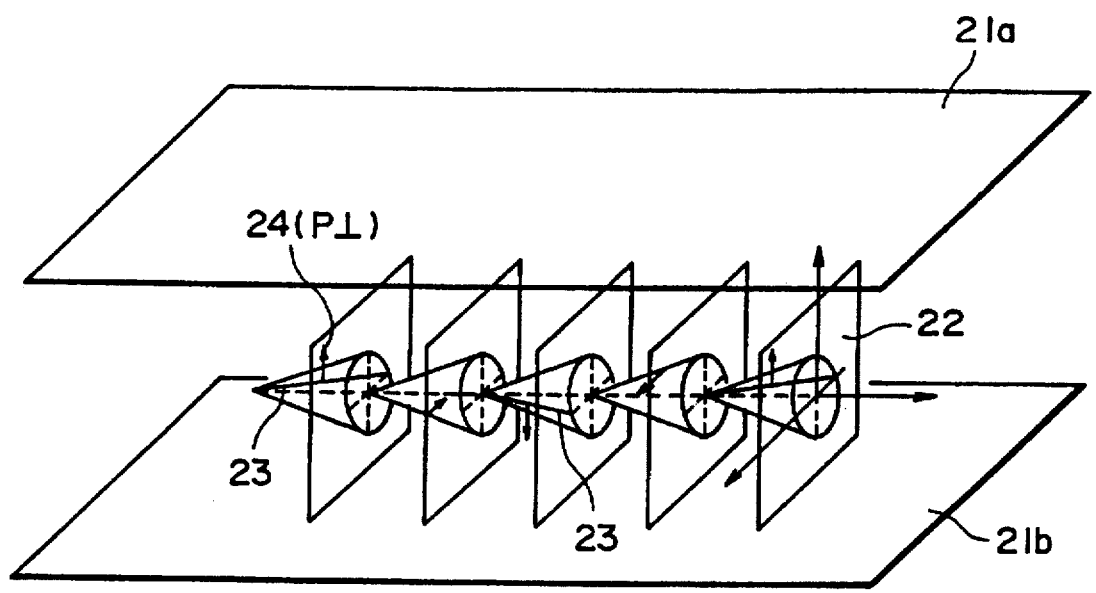
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
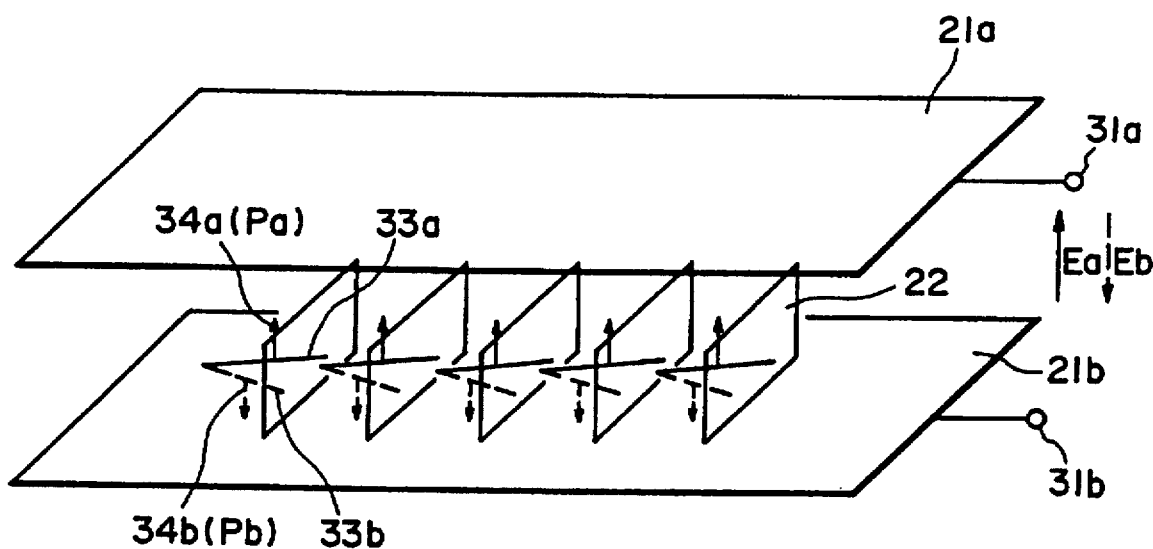

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 5A:
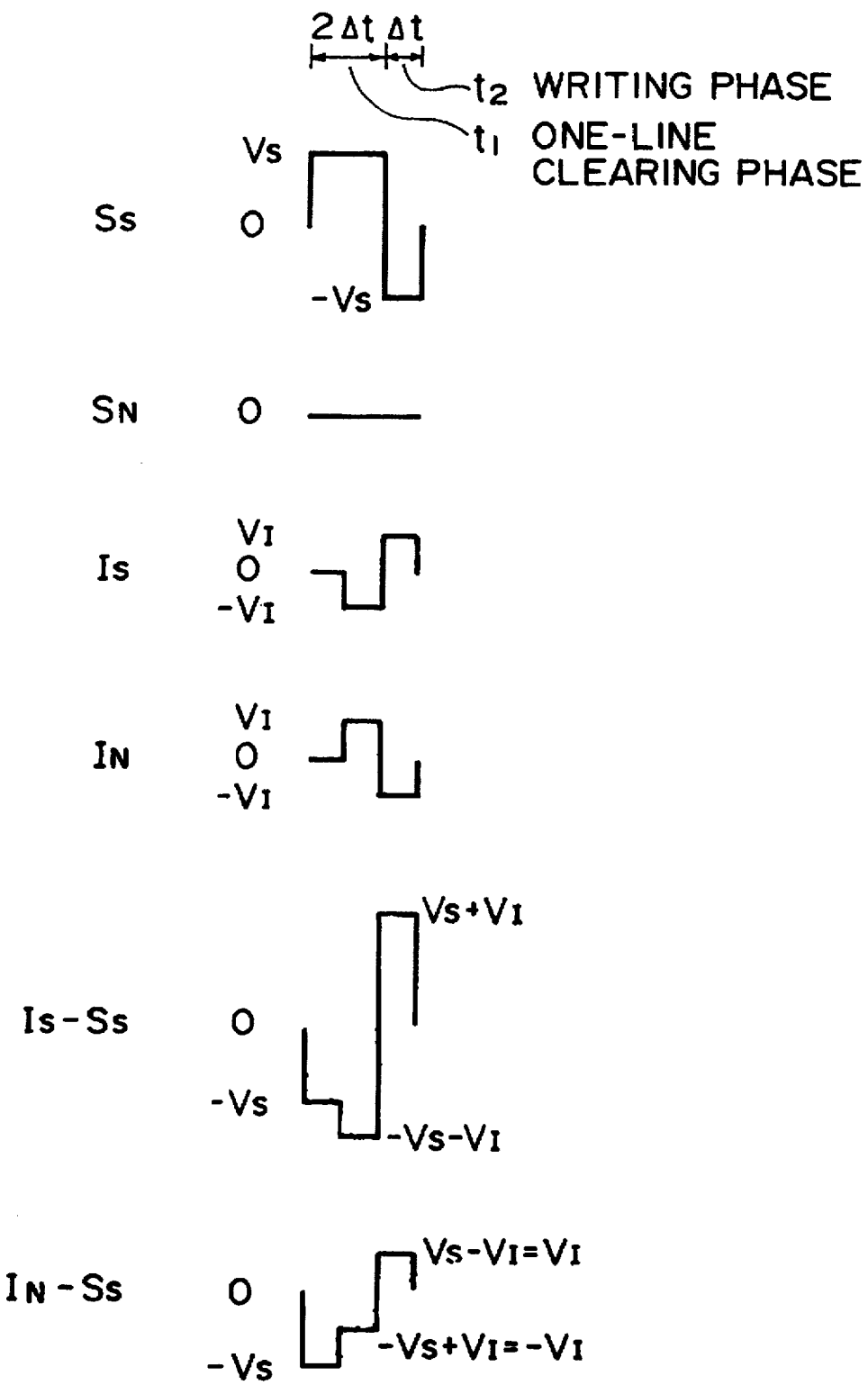
FIG. 5A shows unit driving waveforms used in an embodiment of the present invention.
Figure 5B:
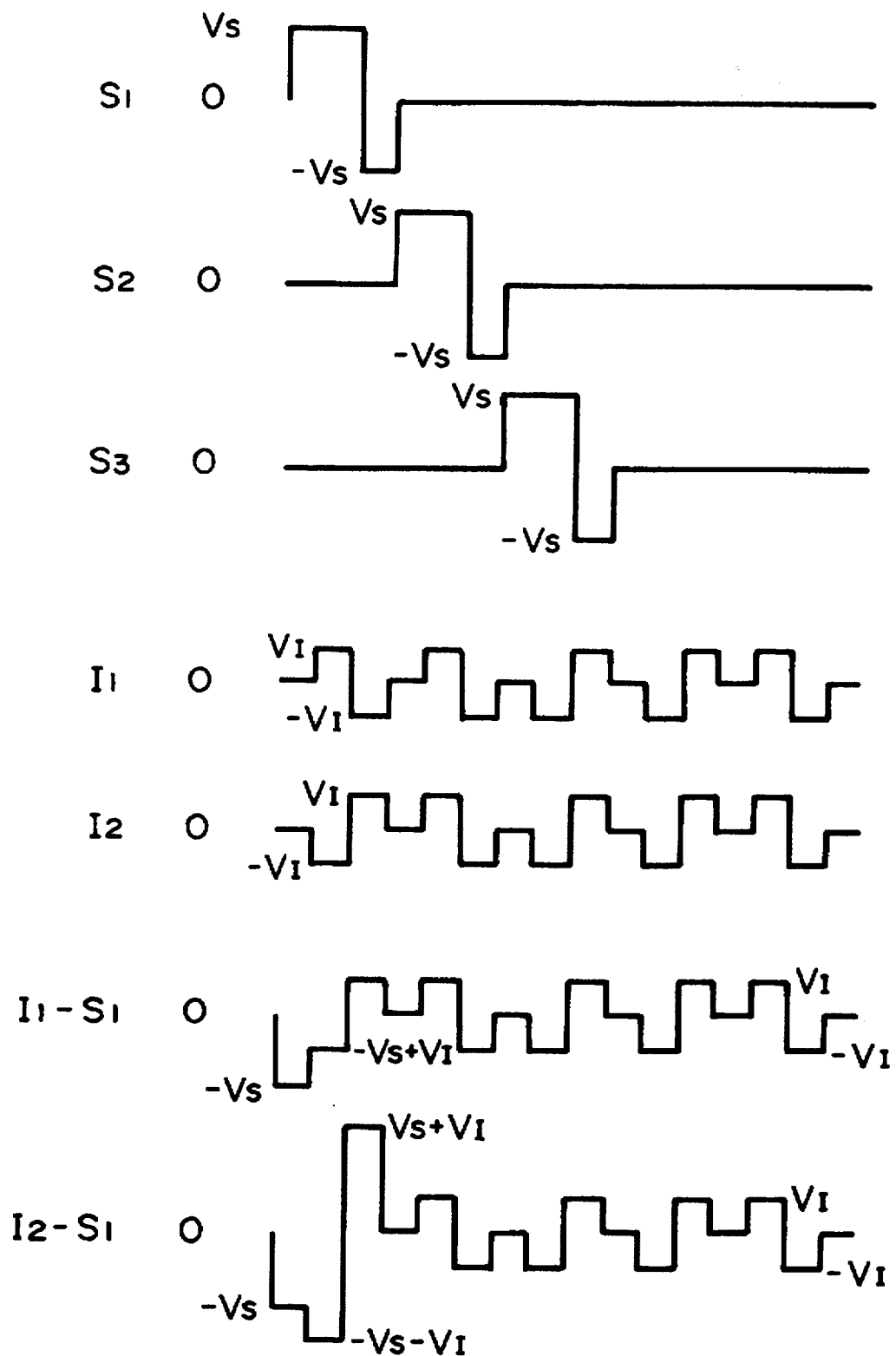
FIG. 5B is time-serial waveforms comprising a succession of such unit waveforms.

FIGS. 5A and 5B are waveform diagrams showing driving voltage waveforms adopted in driving a ferroelectric liquid crystal panel as an embodiment of the liquid crystal device according to the present invention.

Figure 6:
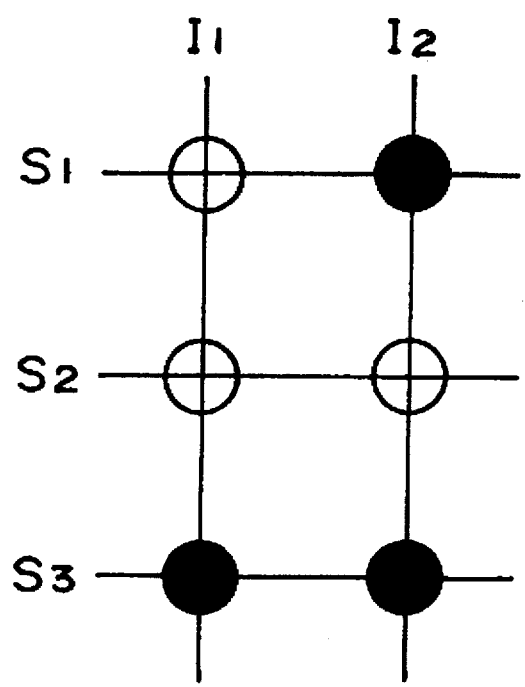
FIG. 6 is an illustration of a display pattern obtained by an actual drive using the time-serial waveforms shown in FIG. 5B.

Referring to FIG. 5A, at $S_S$ is shown a selection scanning signal waveform applied to a selected scanning line, at $S_N$ is shown a non-selection scanning signal waveform applied to a non-selected scanning line, at $I_S$ is shown a selection data signal waveform (providing a black display state) applied to a selected data line, and at $I_N$ is shown a non-selection data signal waveform (providing a white display state) applied to a non-selected data line. Further, at $(I_S-S_S)$ and $(I_N-S_S)$ in the figure are shown voltage waveforms applied to pixels on a selected scanning line, whereby a pixel supplied with the voltage $(I_S-S_S)$ assumes a black display state and a pixel supplied with the voltage $(I_N-S_S)$ assumes a white display state. FIG. 5B shows a time-serial waveform used for providing a display state as shown in FIG. 6.

In the driving waveforms shown in FIGS. 5A and 5B, a minimum duration Δt of a single polarity voltage applied to a pixel on a selected scanning line corresponds to the period of a writing phase $t_2$, and the period of a one-line clearing phase $t_1$ is set to 2Δt.

The parameters $V_S$, $V_I$ and Δt in the driving waveforms shown in FIGS. 5A and 5B are determined depending on switching characteristics of a ferroelectric liquid crystal material used. In this embodiment, the parameters are fixed at a constant value of a bias ratio $V_I/(V_I+V_S)=⅓$. It is of course possible to increase a range of a driving voltage allowing an appropriate matrix drive by increasing the bias ratio. However, a large bias ratio corresponds to a large amplitude of a data signal and leads to an increase in flickering and a lower contrast, thus being undesirable in respect of image quality. According to our study, a bias ratio of about ⅓–¼ was practical.

The liquid crystal device according to the present invention is used as an element, particularly a display element, for various liquid crystal apparatus.

Figure 7:
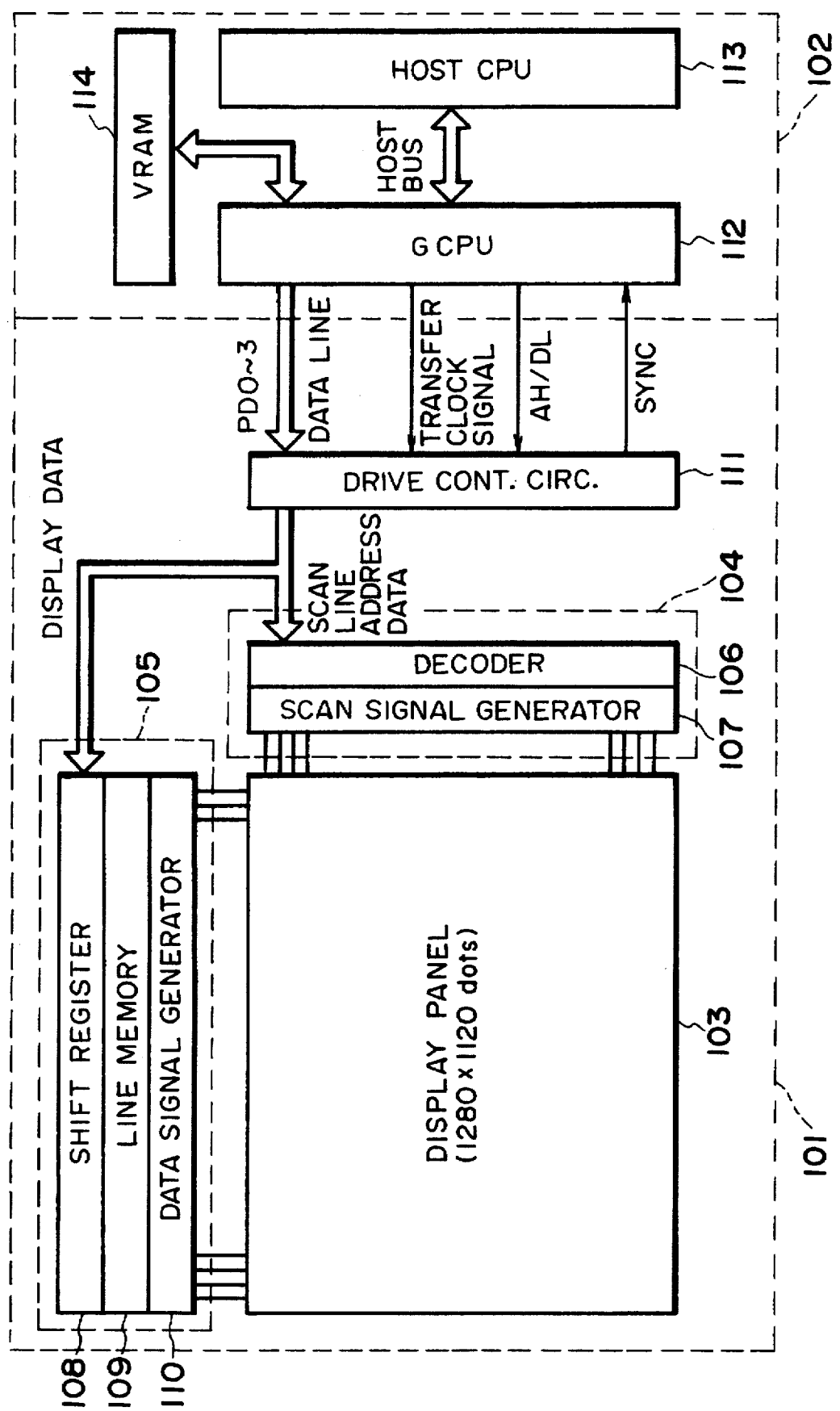
FIG. 7 is a block diagram showing a display apparatus comprising a liquid crystal device utilizing ferroelectricity of a liquid crystal composition and a graphic controller.
Figure 8:
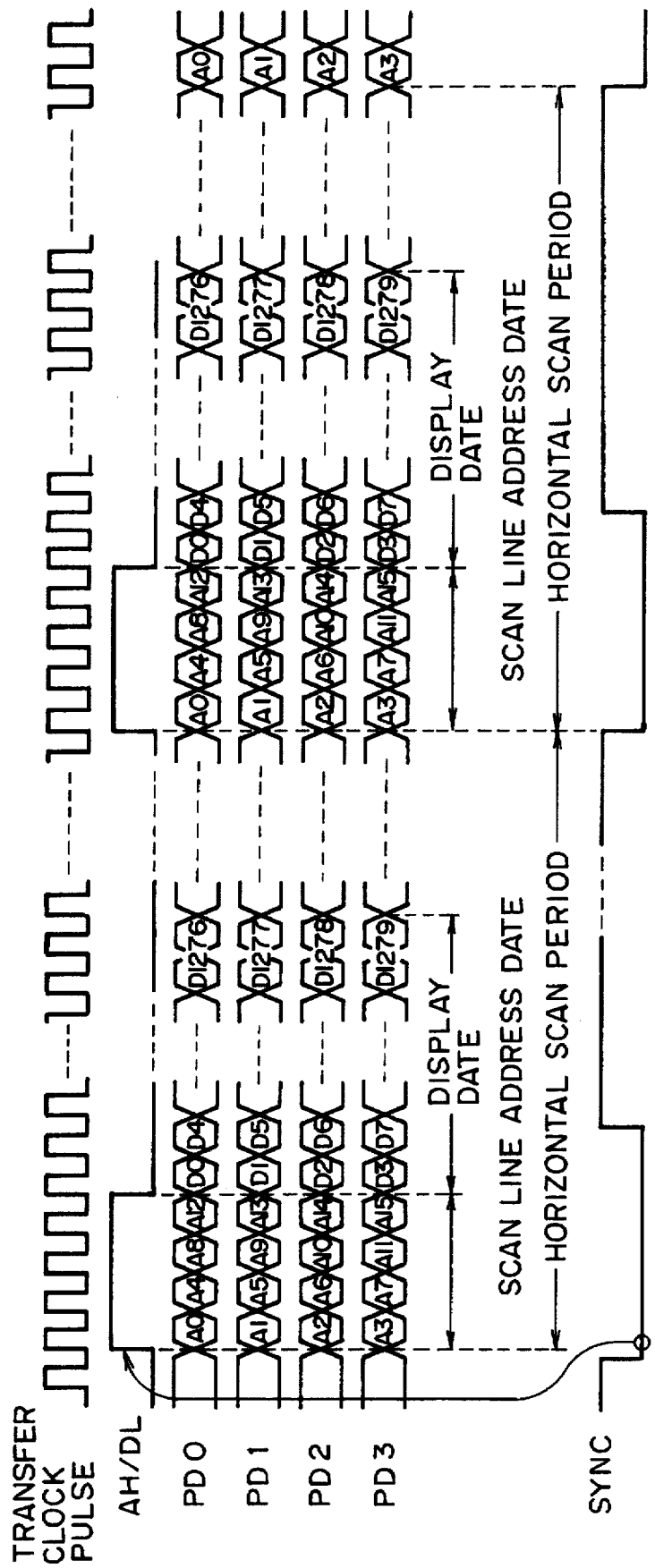
FIG. 8 is a time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization using a SYNC signal as shown in FIGS. 7 and 8, there is provided a liquid crystal display apparatus of the present invention which uses the liquid crystal device according to the present invention as a display panel portion.

Referring to FIG. 7, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally performed by the graphic controller 102. A light source (not shown) is disposed at the back of the display panel 103.

Hereinbelow, the present invention will be explained more specifically with reference to examples. It is however to be understood that the present invention is not restricted to these examples.

EXAMPLE 1

Production of 2-(4-pentylphenyl)-6-methoxyquinoline (Example Compound No. (I-6))

In a 200 ml-three necked flask, 6.45 g (23.5 mM) of 4-pentyliodobenzene and 40 ml of dry tetrahydrofuran (THF) were placed and stirred on a dry ice-acetone bath at −75° to −65° C. (inner temperature) under nitrogen atmosphere. Under stirring, 17.3 ml (27.7 mM) of a solution of 1.6M-butyl-lithium in hexane was added dropwise to the mixture in 15 minutes, followed by stirring for 1 hour at −75° to −65° C.

To the resultant mixture, a solution of 2.18 ml (15.8 mM) of 6-methoxyquinoline in 13 ml of dry THF was added dropwise in 30 minutes at the same temperature. After the addition, the dry ice-acetone bath was removed and the mixture was stirred for 1 hour and 40 minutes at room temperature. After the reaction, the reaction mixture was poured into ice water and subjected to extraction with ethyl acetate. The organic layer was washed with water and dried with anhydrous sodium sulfate, followed by evaporation under reduced pressure to obtain a residue. To the residue, 5 ml of nitrobenzene was added, followed by refluxing under stirring. The reaction mixture was subjected to reduced-pressure distillation to distill off nitrobenzene as much as possible. The resultant crude product was purified by silica gel column chromatography (eluent: toluene/ethyl acetate= 100/1) and recrystallized from methanol to obtain 2.16 g of 2-(4-pentylphenyl)-6-methoxyquinoline (Yield: 44.8%). This compound showed the following phase transition series.

Phase transition temperature (°C.)

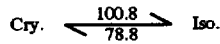

Herein, the respective symbols denote the following phases; Iso.: isotropic phase; Ch: cholesteric phase; N: nematic phase; SmA: smectic A phase; SmC*: chiral smectic C phase; Sm: smectic phase (un-identified); and Cry.: crystal.

EXAMPLE 2

Production of 2-(4-pentylphenyl)-6-decyloxyquinoline (Ex. Comp. No. (I-10))

0.70 g (2.29 mM) of 2-(4-pentylphenyl)-6-methoxyquinoline, 4.6 ml of acetic acid and 4.3 ml of 47%-hydrobromic acid were placed in a 30 ml-round bottomed flask, followed by refluxing for 33 hours under stirring. After the reaction, the reaction mixture was poured into ice water to precipitate a crystal. The crystal was recovered by filtration and dispersed in water. To the mixture, an appropriate amount of ethyl acetate was added, followed by stirring at room temperature. Under stirring, 1.5 g of sodium hydrogencarbonate was gradually added to the resultant mixture. The organic (ethyl acetate) layer was washed with water and dried with anhydrous sodium sulfate, followed by evaporation under reduced pressure to obtain a residue. To the residue, an appropriate amount of hexane was added, followed by filtration to obtain 0.58 g of 2-(4-pentylphenyl)-6-hydroxyquinoline (as a precipitated crystal) (Yield: 86.8%).

Then, 0.23 g (0.79 mM) of 2-(4-pentylphenyl)-6-hydroxyquinoline, 0.17 ml (0.82 mM) of 1-bromodecane and 2.6 ml (0.02 g of potassium hydroxide per 1 ml of butanol) of a solution of potassium hydroxide in butanol were placed in a 20 ml-round bottomed flask and refluxed for 2 hours and 50 minutes under stirring. After the reaction, the reaction mixture was left standing overnight in a freezer at −20° C. to precipitate a crystal. The crystal was recovered by filtration and successively washed with methanol and water. The resultant crystal was purified by silica gel column chromatography (eluent: toluene) and recrystallized from a mixture solvent (toluene and methanol) to obtain 0.23 g of 2-(4-pentylphenyl)-6-decyloxyquinoline (Yield: 67.5%).

Phase transition temperature (°C.)

EXAMPLE 3

A liquid crystal composition A was prepared by mixing the following compounds in the indicated proportions.

| Structural formula | wt. parts |
| --- | --- |
| $C_7H_{15}$—Py2—Ph—$OC_9H_{19}$ | 12 |
| $C_{11}H_{23}$—Py2—Ph—$OC_6H_{13}$ | 10 |
| $C_8H_{17}$—Pr2—Ph—$O(CH_2)_5$*$CH(CH_3)C_2H_5$ | 10 |
| $C_{10}H_{21}$—Py2—Ph—$O(CH_2)_4CH(CH_3)OCH_3$ | 3 |
| $C_6H_{17}$—Py2—Ph—Ph—$OC_6H_{13}$ | 8 |
| $C_6H_{13}O$—Ph—OCO—Np—$OC_9H_{19}$ | 4 |
| $C_3H_7$—Cy—COO—Ph—Py1—$C_{11}H_{23}$ | 6 |
| $C_8H_{17}$—Cy—COO—Ph—Py1—$C_{11}H_{23}$ | 2 |
| $C_5H_{11}$—Cy—COO—Ph—Py1—$C_{11}H_{23}$ | 8 |
| $C_{10}H_{21}O$—Ph—COO—Ph—$OCH_2$*$CH(CH_3)C_2H_5$ | 15 |
| $C_4H_9$—Cy—$CH_2O$—Ph—Py1—$C_6H_{13}$ | 7 |
| $C_5H_{11}$—Cy—$CH_2O$—Ph—Py1—$C_6H_{13}$ | 7 |
| $C_9H_{19}O$—Ph—$OCH_2$—Ph—Ph—$C_7H_{15}$ | 4 |
| $C_6H_{13}$*$CH(CH_3)O$—Ph—COO—Ph—Ph—$OCO$*$CH(CH_3)OC_4H_9$ | 2 |
| $C_{12}H_{25}$—Py2—Ph—$OCO$*$CH(Cl)$*$CH(CH_3)C_2H_5$ | 2 |

In the above, *C denotes an optically active asymmetric carbon atom.

The liquid crystal composition A was further mixed with the following example compounds in the indicated proportions to provide a liquid crystal composition B.

| Ex. Comp. No. | Structural formula | wt. parts |
| --- | --- | --- |
| I-3 | $C_{10}H_{21}$-Q-Ph-$C_5H_{11}$ | 5 |
| I-39 | $C_4H_9$-Q-Ha-$C_6H_{13}$ | 2 |
| I-88 | $C_9H_{19}O$-Q-Ph-F | 2 |
| | Composition A | 91 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm (33 s$^{-1}$) for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm (33 s$^{-1}$) for 15 seconds. Thereafter, the coating film was subjected to heat curing at 300° C. for 60 min. to obtain about 25 nm-thick film. The coating film was rubbed with acetate fiber-planted cloth. The thus treated two glass plates were washed with isopropyl alcohol. After silica beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell.

Then, the liquid crystal composition B prepared above was heated into an isotropic liquid, and injected into the above prepared cell under vacuum and, after sealing, was gradually cooled to 25° C. at a rate of 20° C./hour to prepare a liquid crystal device (ferroelectric liquid crystal device). The cell gap was found to be about 2 microns as measured by a Berek compensator.

The liquid crystal device was subjected to measurement of an optical response time (time from voltage application until the transmittance change reaches 90% of the maximum under the application of a peak-to-peak voltage Vpp of 20 V in combination with right-angle cross-nicol polarizers) and evaluation of a temperature-dependence of response time (i.e., a ratio of a response time at low temperature to a response time at high temperature). The results of the measurement are shown below.

| | 10° C. | 25° C. | 40° C. |
| --- | --- | --- | --- |
| Response time (μsec) | 627 | 310 | 171 |
| Ratio (10° C./40° C.) | 3.7 | | |

Comparative Example 1

A liquid crystal device was prepared and evaluated in the same manner as in Example 3 except for injecting the composition A alone used in Example 3 into a blank cell, whereby the following results were obtained.

| | 10° C. | 25° C. | 40° C. |
| --- | --- | --- | --- |
| Response time (μsec) | 784 | 373 | 197 |
| Ratio (10° C./40° C.) | 4.0 | | |

EXAMPLE 4

A liquid crystal composition C was prepared by mixing the following Example Compounds instead of those (I-3), (I-39) and (I-88) used in Example 3 in the indicated proportions with the liquid crystal composition A.

| Ex. Comp. No. | Structural formula | wt. parts |
| --- | --- | --- |
| I-13 | $C_6H_{13}COO$-Q-Ph-$C_{10}H_{21}$ | 3 |
| I-31 | $C_8H_{17}$-Q-Id-$C_8H_{17}$ | 2 |
| I-49 | $C_6H_{13}$-Q-Pyl-$C_6H_{13}$ | 4 |
| | Composition A | 91 |

A liquid crystal device was prepared in the same manner as in Example 3 except that the above liquid crystal composition C was used, and the device was subjected to measurement of optical response time, evaluation of a temperature-dependence of response time and observation of switching states. In the device, a monodomain with a good and uniform alignment characteristic was observed. The results of the measurement and evaluation are shown below.

|  | 10° C. | 25° C. | 40° C. |
|---|---|---|---|
| Response time (μsec) | 605 | 304 | 168 |
| Ratio (10° C./40° C.) | 3.6 | | |

EXAMPLE 5

A liquid crystal composition D was prepared by mixing the following compounds in the indicated proportions.

| Structural formula | wt. parts |
|---|---|
| $C_8H_{17}$—Py2—Ph—$OC_6H_{13}$ | 10 |
| $C_8H_{17}$—Py2—Ph—$OC_9H_{19}$ | 5 |
| $C_{10}H_{21}$—Py2—Ph—$OCOC_6H_{13}$ | 7 |
| $C_{10}H_{21}$—Py2—Ph—$O(CH_2)_2CH(CH_3)OC_3H_7$ | 7 |
| $C_{12}H_{25}$—Py2—Ph—$O(CH_2)_4CH(CH_3)OCH_3$ | 6 |
| $C_5H_{11}$—Py2—Ph—Ph—$C_6H_{13}$ | 5 |
| $C_7H_{15}$—Py2—Ph—Ph—$C_6H_{13}$ | 5 |
| $C_4H_9$—Cy—COO—Ph—Py1—$C_{12}H_{25}$ | 8 |
| $C_3H_7$—Cy—COO—Ph—Py1—$C_{10}H_{21}$ | 8 |
| $C_8H_{19}$—Ph—COO—Ph—$OC_5H_{11}$ | 20 |
| $C_8H_{17}$—Ph—COO—Ph—Ph—$OCH_2CH(CH_3)C_2H_5$ | 5 |
| $C_8H_{17}$—Ph—OCO—Ph—Ph—*$CH(CH_3)OCOC_6H_{13}$ | 5 |
| $C_6H_{13}O$—Ph—$OCH_2$—Ph—Ph—$C_7H_{15}$ | 6 |
| $C_{12}H_{25}$—Py2—Ph—$OCH_2$*$CH(F)C_6H_{13}$ | 3 |

In the above, *C denotes an optically active asymmetric carbon atom.

The liquid crystal composition D was further mixed with the following compounds in the proportions indicated below to provide a liquid crystal composition E.

| Ex. Comp. No. | Structural formula | wt. parts |
|---|---|---|
| I-18 | $C_8H_{17}$*$CH(F)CH_2O$-Q-Ph-$C_7H_{15}$ | 2 |
| I-25 | $C_9H_{19}$-Q-Tn-$C_5H_{11}$ | 4 |
| I-62 | $C_{12}H_{25}O$-Q-Cy-$C_3H_7$ | 2 |
| | Composition D | 92 |

A liquid crystal device was prepared in the same manner as in Example 3 except that the above liquid crystal composition E was used, and the device was subjected to measurement of optical response time, evaluation of a temperature-dependence of response time and observation of switching states. In the device, a monodomain with a good and uniform alignment characteristic was observed. The results of the measurement and evaluation are shown below.

|  | 10° C. | 25° C. | 40° C. |
|---|---|---|---|
| Response time (μsec) | 525 | 265 | 142 |
| Ratio (10° C./40° C.) | 3.7 | | |

Comparative Example 2

A liquid crystal device was prepared and subjected to measurement of response time in the same manner as in Example 3 except for injecting the composition D alone used in Example 5 into a blank cell, whereby the following results were obtained.

|  | 10° C. | 25° C. | 40° C. |
|---|---|---|---|
| Response time (μsec) | 653 | 317 | 159 |
| Ratio (10° C./40° C.) | 4.1 | | |

EXAMPLE 6

A liquid crystal composition F was prepared by mixing the following Example Compounds instead of those (I-18), (I-25) and (I-62) used in Example 5 in the indicated proportions with the liquid crystal composition D.

| Ex. Comp. No. | Structural formula | wt. parts |
|---|---|---|
| I-35 | $C_8H_{17}$-Q-Ph-Cm-$C_8H_{17}$ | 2 |
| I-56 | $C_{11}H_{23}O$-Q-Prl-$C_6H_{13}$ | 4 |
| I-71 | $C_9H_{19}$-Q-Ph3F-$C_5H_{11}$ | 3 |
| | Composition D | 91 |

A liquid crystal device was prepared in the same manner as in Example 3 except that the above liquid crystal composition F was used, and the device was subjected to measurement of optical response time, evaluation of a temperature-dependence of response time and observation of switching states. In the device, a monodomain with a good and uniform alignment characteristic was observed. The results of the measurement and evaluation are shown below.

|  | 10° C. | 25° C. | 40° C. |
|---|---|---|---|
| Response time (μsec) | 530 | 271 | 144 |
| Ratio (10° C./40° C.) | 3.7 | | |

As apparent from the above Examples 3 to 6, the liquid crystal devices including the liquid crystal compositions B, C, E and F, i.e., compositions containing a mesomorphic compound of the formula (I) according to the present invention, provided improved operation characteristic at a lower temperature, high speed responsiveness and a decreased temperature-dependence of response speed.

EXAMPLE 7

A blank cell was prepared in the same manner as in Example 3 by using a 2% aqueous solution of polyvinyl alcohol resin (PVA-117, available from Kuraray K.K.) instead of the 1.5%-solution of polyimide resin precursor in dimethylacetoamide on each electrode plate. A liquid crystal device was prepared by filling the blank cell with the liquid crystal composition B used in Example 3. The liquid crystal device was subjected to measurement response time and evaluation of a temperature-dependence of response time in the same manner as in Example 3. The results are shown below.

|  | 10° C. | 25° C. | 40° C. |
|---|---|---|---|
| Response time (μsec) | 630 | 312 | 175 |
| Ratio (10° C./40° C.) | 3.6 | | |

EXAMPLE 8

A blank cell was prepared in the same manner as in Example 3 except for omitting the $SiO_2$ layer to form an alignment control layer composed of the polyimide resin layer alone on each electrode plate. A liquid crystal devices were prepared by filling such a blank cell with liquid crystal composition B used in Example 3. The liquid crystal device was subjected to measurement of response time and evaluation of a temperature-dependence of response time in the same manner as in Example 3. The results are shown below.

|  | 10° C. | 25° C. | 40° C. |
|---|---|---|---|
| Response time (µsec) | 592 | 292 | 160 |
| Ratio (10° C./40° C.) | 3.7 | | |

As is apparent from the above Examples 7 and 8, also in the case of a different device structure, the device containing the ferroelectric liquid crystal composition B according to the present invention provided an improved low-temperature operation characteristic and a decreased temperature dependence of response speed similarly as in Example 3.

EXAMPLE 9

A liquid crystal composition G was prepared by mixing the following compounds in the indicated proportions.

| Structural formula | wt. parts |
|---|---|
| $C_9H_{19}$—Py2—Ph—$OC_{10}H_{21}$ | 5 |
| $C_{10}H_{21}$—Py2—Ph—$OC_9H_{19}$ | 10 |
| $C_8H_{17}O$—Pr1—Ph—$O(CH_2)_5CH(CH_3)C_2H_5$ | 5 |
| $C_{10}H_{21}$—Py2—Ph—$O(CH_2)_4CH(CH_3)OCH_3$ | 10 |
| $C_6H_{13}$—Py2—Ph—Ph—$C_8H_{17}$ | 7 |
| $C_6H_{17}$—Py2—Ph—$OC_6H_{13}$ | 15 |
| $C_5H_{11}$—Cy—COO—Ph—Py1—$C_{12}H_{25}$ | 5 |
| $C_4H_9$—Cy—COO—Ph—Py1—$C_{11}H_{23}$ | 5 |
| $C_3H_7$—Cy—COO—Ph—Py1—$C_{11}H_{23}$ | 5 |
| $C_{12}H_{25}O$—Ph—Pa—$CO(CH_2)_3$*$CH(CH_3)C_2H_5$ | 2 |
| $C_{10}H_{21}$—Py2—Ph—$OCH_2$*$CH(F)C_2H_5$ | 5 |
| $C_6H_{13}$—Cy—COO—Ph—$OCH_2$*$CH(F)C_6H_{13}$ | 2 |
| $C_8H_{17}$—Ph—OCO—Ph—Ph—$CH(CH_3)OCOC_6H_{13}$ | 6 |
| $C_8H_{17}$—Py2—Ph—OCO—Ph—F | 2 |
| $C_7H_{15}O$—Ph—Tz—Ph—$C_5H_{11}$ | 3 |
| $C_6H_{13}O$—Bt—Ph—$OCOC_4H_9$ | 3 |
| $C_{10}H_{21}O$—Ph—COS—Ph—$OC_8H_{17}$ | 10 |

In the above, *C denotes an optically active asymmetric carbon atoms.

The liquid crystal composition G was further mixed with the following example compounds in the indicated proportions to provide a liquid crystal composition H.

| Ex. Comp. No. | Structural formula | wt. parts |
|---|---|---|
| I-9 | $C_9H_{19}$-Q-Ph-$C_8H_{17}$ | 3 |
| I-10 | $C_{10}H_{21}$-O-Q-Ph-$C_5H_{11}$ | 4 |
| I-63 | $C_9H_{19}$-Q-NP-$C_{10}H_{21}$ | 3 |
| | Composition G | 90 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm (33 $s^{-1}$) for 15 second and subjected to hot curing treatment at 120° C. for 20 min.

Further, each glass plate provided with an ITO film and treated in the above described manner was coated with a 1.0%-solution of polyimide resin precursor (SP-510, available from Toray K.K.) in dimethylacetoamide by a spinner coater rotating at 3000 rpm for 15 seconds. Thereafter, the coating film was subjected to heat curing at 300° C. for 60 min. to obtain about 12 nm-thick film. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell.

Then, the liquid crystal composition H prepared above was heated into an isotropic liquid, and injected into the above prepared cell under vacuum and, after sealing, was gradually cooled to 25° C. at a rate of 20° C./hour to prepare a liquid crystal device (FLC device). The cell gap was found to be about 1.5 µm as measured by a Berek compensator.

The liquid crystal device was subjected to measurement of a contrast ratio at 30° C. when the device was driven by applying a driving voltage waveform shown in FIGS. 5A and 5B (bias ratio=⅓), whereby a contrast ratio at 30° C. of 25.5 was obtained.

Comparative Example 3

A ferroelectric liquid crystal device was prepared and subjected to measurement of a contrast ratio in the same manner as in Example 9 except for injecting the composition G alone used in Example 9 into a blank cell, whereby a contrast ratio at 30° C. of 6.7 was obtained.

EXAMPLE 10

A liquid Crystal composition J was prepared by mixing the following Example Compounds instead of those (I-9), (I-10) and (I-63) used in Example 9 in the indicated proportions with the liquid crystal composition G.

| Ex. Comp. No. | Structural formula | wt. parts |
|---|---|---|
| I-4 | $C_{11}H_{23}$-Q-Ph-$C_8H_{17}$ | 3 |
| I-50 | $C_8H_{17}$O-Q-Py1-$C_9H_{19}$ | 3 |
| I-85 | $C_{12}H_{25}$O-Q-Ph3F-F | 2 |
| | Composition G | 92 |

A liquid crystal device was prepared in the same manner as in Example 9 except that the above liquid crystal composition J was used, and the device was subjected to measurement of a contrast ratio, whereby a contrast ratio at 30° C. of 21.4 was obtained.

As apparent from the above Examples 9 and 10, the liquid crystal devices including the liquid crystal compositions H and J, i.e., compositions containing a mesomorphic compound of the formula (I) according to the present invention, provided improved a higher contrast ratio when driven.

EXAMPLE 11

A blank cell was prepared in the same manner as in Example 9 by using a 2% aqueous solution of polyvinyl alcohol resin (PVA-117, available from Kuraray K.K.) instead of the 1.0%-solution of polyimide resin precursor in dimethylacetoamide on each electrode plate. A liquid crystal device was prepared by filling the blank cell with the liquid crystal composition H used in Example 9. The liquid crystal device was subjected to measurement a contrast ratio in the same manner as in Example 9, whereby a contrast ratio at 30° C. of 28.0 was obtained.

EXAMPLE 12

A blank cell was prepared in the same manner as in Example 9 except for omitting the $SiO_2$ layer to form an alignment control layer composed of the polyimide resin layer alone on each electrode plate. A liquid crystal devices were prepared by filling such a blank cell with liquid crystal composition H used in Example 9. The liquid crystal device was subjected to measurement of response time in the same manner as in Example 9, whereby a contrast ratio at 30° C. of 20.6 was obtained.

EXAMPLE 13

A blank cell was prepared in the same manner as in Example 9 except that a 1.0%-solution of polyamide acid (LQ-1802, available from Hitachi Kasei K.K.) in NMP (N-methylpyrrolidone) instead of the 1.0%-solution of polyimide resin precursor in dimethylacetoamide was formed on each electrode plate. A liquid crystal device was prepared by filling the blank cell with the liquid crystal composition H used in Example 9. The liquid crystal device was subjected to measurement a contrast ratio in the same manner as in Example 9, whereby a contrast ratio of 37.9 was obtained.

As is apparent from the above Examples 11, 12 and 13, also in the case of a different device structure, the device containing the liquid crystal composition H according to the present invention provided a higher contrast ratio similarly as in Example 9.

Further, when a driving voltage waveform different from that used in Example 9 was used, liquid crystal devices using the liquid crystal compositions according to the present invention provided a higher contrast ratio compared with liquid crystal devices using liquid crystal compositions containing no mesomorphic compound of the formula (I) of the present invention.

EXAMPLE 14

A liquid crystal composition K was prepared by mixing the following compounds in the indicated proportions.

| Structural formula | wt. parts |
| --- | --- |
| $C_6H_{13}$—Py2—Ph—$OC_{12}H_{25}$ | 4.0 |
| $C_8H_{17}$—Py2—Ph—$OC_9H_{19}$ | 8.0 |
| $C_8H_{17}$—Py2—Ph—$OC_{10}H_{21}$ | 8.0 |
| $C_9H_{19}$—Py2—Ph—$OC_8H_{17}$ | 4.0 |
| $C_{10}H_{21}O$—Ph—COO—Ph—$OCH_2CH(CH_3)CH_2H_5$ | 16.0 |
| $C_6H_{13}$—Btb2—Ph—$OC_8H_{17}$ | 20.0 |
| $C_5H_{11}$—Ph—Td—Ph—$C_5H_{11}$ | 5.0 |
| $C_6H_{13}$—Ph—Td—Ph—$C_4H_9$ | 5.0 |
| $C_{11}H_{23}$—Py—Ph—OCO—Tn—$C_4H_9$ | 6.7 |
| $C_{11}H_{23}$—Py—Ph3F—OCO—Tn—$C_4H_9$ | 3.3 |
| $C_{10}H_{21}$—Py2—Ph—$OCH_2$*$CH(F)C_6H_{13}$ | 10.0 |
| Ex. Comp. No. (I-10) $C_{10}H_{21}O$—Q—Ph—$C_5H_{11}$ | 5.0 |

In the above, Td means thiadiazole-2,5-diyl. The liquid crystal composition K showed the following phase transition series.

Phase transition temperature (°C.)

A liquid crystal device was prepared in the same manner as in Example 3 except that the above liquid crystal composition K was used, and the device was subjected to measurement of optical response time and evaluation of a temperature-dependence of response time. The results of the measurement and evaluation are shown below.

|  | 15° C. | 35° C. | 55° C. |
| --- | --- | --- | --- |
| Response time (μsec) | 140 | 58 | 21 |
| Ratio (15° C./55° C.) | 6.7 | | |

Comparative Example 4

Production of 6-decyl-2-(4-pentylphenyl) quinoline 6-decyl-2-(4-pentylphenyl)quinoline was synthesized through the following reaction steps 1–4.

(Step 1) Production of 6-decylquinoline 12.5 g of 6-decylaniline, 5.0 g of 3-nitrobenzenesulfonic acid, 1.5 g of iron (II) sulfide, 10 ml of sulfuric acid, and 2.8 g of boric acid were dissolved in 13 ml of glycerin (glycerol), followed by stirring for 6 hours at 140° C. After the reaction, the reaction mixture was poured into water and alkalinized by adding thereto an appropriately amount of sodium hydroxide aqueous solution, followed by extraction with diethyl ether. The organic layer was washed with water, dried with anhydrous sodium sulfate and subjected to distilling-off of the solvent, followed by purification by silica gel column chromatography to obtain 2.0 g of 6-decylquinoline.

(Step 2) Production of 6-decyl-2-(4-methoxyphenyl) quinoline

To a solution of 3.5 g of 4-bromoanisole in 7 ml of dry benzene, 11 ml of 1.6 (mol/l)-butyl-lithiumhexane solution was added, followed by stirring overnight at room temperature. After the reaction, the solvent was removed from the reaction mixture by decantation to obtain a solid. The solid was sufficiently dried, dissolved in dry THF and cooled on an ice bath to 0° C. To the solution, a solution of 1.8 g of 6-decylquinoline in 12 ml of dry THF was added, followed by stirring for 2 hours. After the reaction, the reaction mixture after restored to room temperature was further stirred for 1 hour and then poured into water, followed by extraction with diethyl ether. The organic layer was washed with water, dried with anhydrous sodium sulfate and subjected to distilling-off of the solvent, followed by purification by silica gel column chromatography and recrystallization to obtain 2.5 g of 6-decyl-2-(4-methoxyphenyl) quinoline.

(Step 3) Production of 6-decyl-2-(4-hydroxyphenyl) quinoline

To 35 ml of acetic acid, 2.5 g of 6-decyl-2-(4-methoxyphenyl)quinoline and 15 ml of 47%-hydrobromic acid were added, followed by stirring for 12 hours at 100° C. and further stirring overnight at room temperature. After the reaction, the reaction mixture was poured into water and subjected to extraction with chloroform. The organic layer was washed with water and dried with anhydrous sodium sulfate, followed by distilling-off of the solvent and purification by silica gel column chromatography to obtain 1.7 g of 6-decyl-2-(4-hydroxyphenyl)quinoline.

(Step 4) Production of 6-decyl-2-(4-pentyloxyphenyl) quinoline

To a solution 0.8 g of 6-decyl-2-(4-hydroxyphenyl) quinoline and 170 mg potassium hydroxide in 12 ml of butanol, 0.5 g of pentyl bromide was added, followed by heat refluxing for 4 hours. After the reaction, the reaction mixture was poured into water and subjected to extraction with toluene. The organic layer was washed with water, dried with anhydrous sodium sulfate and subjected to distilling-off of the solvent, followed by purification by silica gel column chromatography and recrystallization to obtain 0.8 g of 6-decyl-2-(4-pentyloxyphenyl)quinoline. This compound showed the following phase transition series.

Phase transition temperature (°C.)

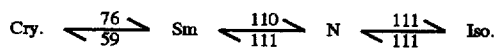

Figure 9:
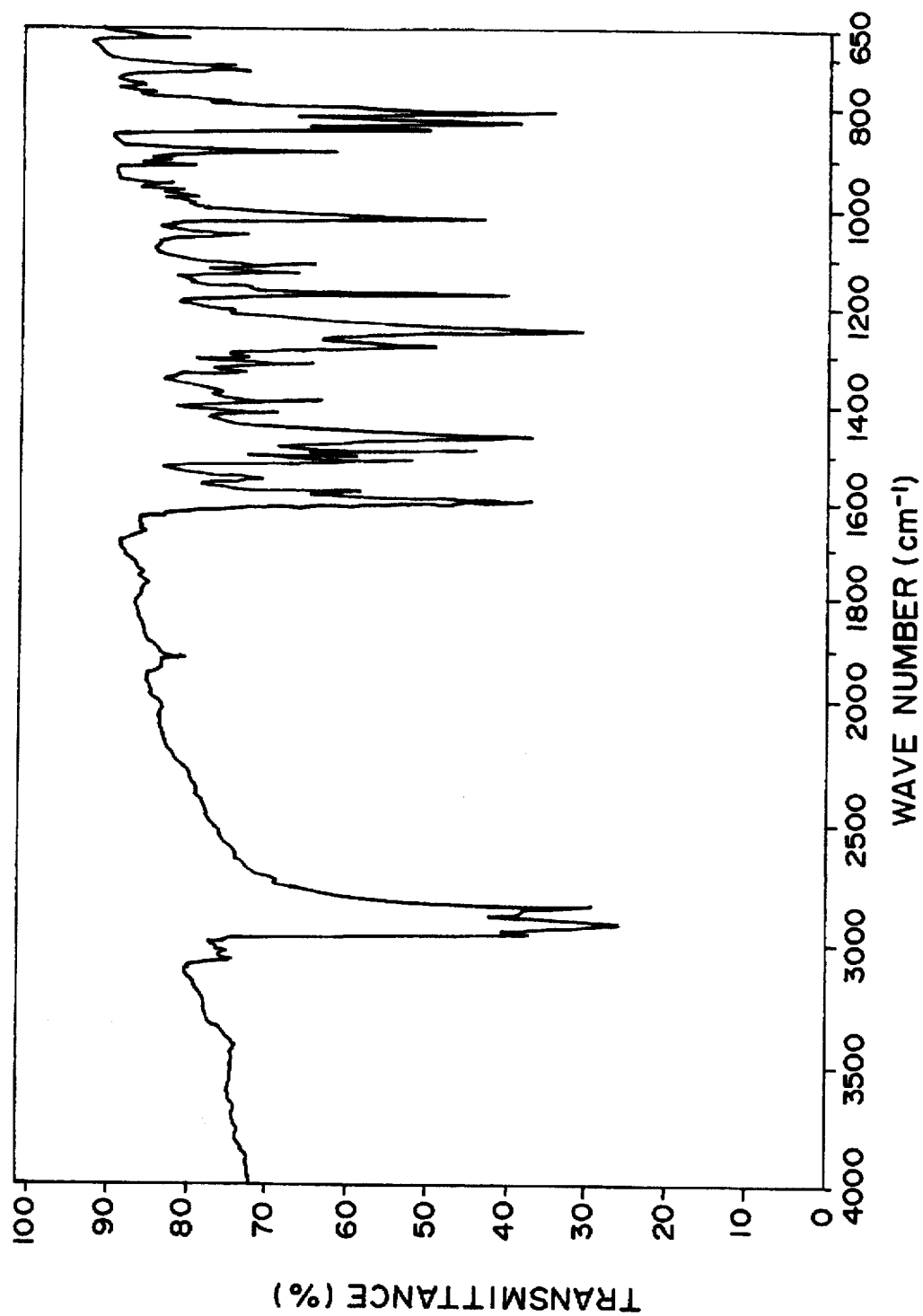
FIG. 9 is a chart showing infrared spectrum (IR chart) of 6-decyl-2-(4-pentyloxyphenyl)quinoline used in Comparative Example 4 appearing hereinafter.

The above-prepared 6-decyl-2-(4-pentylphenyl)quinoline provided an IR chart shown in FIG. 9.

A liquid crystal composition L was prepared in the same manner as in Example 14 except that the mesomorphic compound (Ex. Comp. No. (I-10)) was changed to the above-prepared 6-decyl-2-(4-pentyloxyphenyl)quinoline as follows.

| Structural formula | wt. parts |
| --- | --- |
| $C_6H_{13}$—Py2—Ph—$OC_{12}H_{25}$ | 4.0 |
| $C_8H_{17}$—Py2—Ph—$OC_9H_{19}$ | 8.0 |
| $C_8H_{17}$—Py2—Ph—$OC_{10}H_{21}$ | 8.0 |
| $C_9H_{19}$—Py2—Ph—$OC_8H_{17}$ | 4.0 |
| $C_{10}H_{21}O$—Ph—COO—Ph—$OCH_2CH(CH_3)C_2H_5$ | 16.0 |
| $C_6H_{13}$—Btb2—Ph—$OC_8H_{17}$ | 20.0 |
| $C_5H_{11}$—Ph—Td—Ph—$C_5H_{11}$ | 5.0 |
| $C_6H_{13}$—Ph—Td—Ph—$C_4H_9$ | 5.0 |
| $C_{11}H_{23}$—Py—Ph—OCO—Tn—$C_4H_9$ | 6.7 |
| $C_{11}H_{23}$—Py—Ph3F—OCO—Tn—$C_4H_9$ | 3.3 |
| $C_{10}H_{21}$—Py2—Ph—$OCH_2$*CH(F)$C_6H_{13}$ | 10.0 |
| (Comparative) $C_{10}H_{21}$—Q—Ph—$OC_5H_{11}$ | 5.0 |

In the above, Td means thiadiazole-2,5-diyl.

The liquid crystal composition K showed the following phase transition series.

Phase transition temperature (°C.)

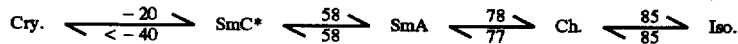

A liquid crystal device was prepared in the same manner as in Example 3 except that the above liquid crystal composition L was used, and the device was subjected to measurement of optical response time and evaluation of a temperature-dependence of response time. The results of the measurement and evaluation are shown below.

|  | 15° C. | 35° C. | 55° C. |
| --- | --- | --- | --- |
| Response time (μsec) | 170 | 66 | 22 |
| Ratio (15° C./55° C.) | 7.7 | | |

The liquid crystal composition for use in a display element (or device) is generally required to have a decreased temperature-dependence of response speed. As apparent from the results of Example 14 and Comparative Example 4, the liquid crystal device using the liquid crystal composition K according to the present invention provided an improved temperature-dependence of response speed and a higher responsiveness (a small decrease in response time) particularly at low temperature (15° C.) when compared with the liquid crystal device using the conventional liquid crystal composition L.

As described hereinabove, according to the present invention, by utilizing a ferroelectricity exhibited by a (chiral smectic) liquid crystal composition containing at least one mesomorphic compound of the formula (I), there is provided a liquid crystal device providing improved characteristic such as a good alignment characteristic, a good switching property, high-speed responsiveness, a decreased temperature-dependence of response speed, and a high contrast ratio.

In addition, when the liquid crystal device is used as a display device in combination with a light source, drive circuit, etc., a liquid crystal apparatus, such as a liquid crystal display apparatus, providing good display characteristics can be realized.

What is claimed is:

1. A liquid crystal composition having a chiral smectic phase, comprising at least two compounds, at least one of which is a mesomorphic compound represented by the following formula (I):

$$R_1\text{-}Q\text{-}A_1 \qquad (I),$$

wherein

Q is quinoline-2,6-diyl;

$A_1$ denotes —$A_2$—$R_2$ or —$A_3$—$R_3$ in which $A_2$ denotes 1,4-phenylene capable of having one or two substituents selected from F, Cl, $CH_3$, $CF_3$ and CN; thiophene-2,5-diyl; indan-2,5-diyl; 2-alkylindan-2,5-diyl having a linear or branched alkyl group having 1–18 carbon atoms; coumaran-2,5-diyl; 2-alkylcoumaran-2,5-diyl having a linear or branched alkyl group having 1–18 carbon atoms; benzofuran-2,5-diyl; or benzofuran-2,6-diyl;

$A_3$ denotes pyrimidine-2,5-diyl; pyridine-2,5-diyl; pyrazine-2,5-diyl; pyridazine-3,6-diyl; 1,4-cyclohexylene; 2,6-naphthylene; quinoxaline-2,6-diyl; or quinoline-2,6-diyl;

$R_1$ and $R_3$ independently denote F, CN, $CF_3$, or a linear, branched or cyclized alkyl group having 1–20 carbon atoms capable of including at least one —$CH_2$— group which can be replaced with —O—, —S—, —CO—, —*$CY_1(Y_2)$—, —CH=CH— or —C≡C— provided that heteroatoms are not adjacent to each other and capable of including at least one —$CH_3$ group which can be replaced with —$CH_2F$, —$CHF_2$ or —CN; in which $Y_1$ and $Y_2$ independently denote H, F, $CH_2F$, $CHF_2$, $CF_3$, CN or a linear alkyl group having 1–5 carbon atoms; and *C denotes an asymmetric carbon atom; and $R_2$ denotes F, CN, $CF_3$, or a linear, branched or cyclized alkyl group having 1–20 carbon atoms capable of including at least one —$CH_2$— group which can be replaced with —*$CY_1(Y_2)$—, —CH=CH— or —C≡C— and capable of including at least one —CH₃ group which can be replaced with —CH₂F, —CHF₂ or —CN.

2. A composition according to claim 1, wherein said at least one of a mesomorphic compound of the formula (I) satisfies at least one of the following conditions (a)–(c):

(a) R₁ is any one of the groups (1)–(5) shown below,
(b) R₂ is any one of the groups (6)–(9) shown below, and
(c) R₃ is any one of the groups (1)–(5) shown below, (1) n-C$_a$H$_{2a+1}$—Y₃—, (2) C$_b$H$_{2b}$CH(CH₃)(CH₂)$_d$—Y₃—, (3) C$_e$H$_{2e+1}$O(CH₂)$_f$CH(CH₃)(CH₂)$_g$—Y₃—, (4) C$_j$H$_{2j+1}$—CHF—Y₄—, (5) C$_h$H$_{2h+1}$—CH(CH₃)CH₂—Y₄—;

(6) n-C$_a$H$_{2a+1}$—, (7) C$_b$H$_{2b+1}$CH(CH₃)(CH₂)$_d$—, (8) C$_j$H$_{2j+1}$—CHFCH₂—, and (9) C$_h$C$_{2h+1}$CH(CF₃)CH₂CH₂—, wherein a is an integer of 1–16; d and g independently denote an integer of 0–7; b, e, h and j independently denote an integer of 1–10; f is 0 or 1, with the proviso that b+d≦16 and e+f+g≦16; Y₃ is a single bond, —O—, —OCO— or —COO—; and Y₄ is —CH₂O—, —CH₂— or —COO—.

3. A composition according to claim 1, wherein A₁ is —A₂—R₂.

4. A composition according to claim 3, wherein A₂ is 1,4-phenylene.

5. A composition according to claim 2, wherein R₁ is the group (1) and R₂ is the group (6).

6. A composition according to claim 1, wherein said at least one of a mesomorphic compound of the formula (I) is 2-(4-pentylphenyl)-6-methoxyquinoline.

7. A composition according to claim 1, wherein said at least one of a mesomorphic compound of the formula (I) is 2-(4-pentylphenyl)-6-decyloxyquinoline.

8. A liquid crystal composition according to claim 1, which comprises 1–80 wt. % of a mesomorphic compound of the formula (I).

9. A liquid crystal composition according to claim 1, which comprises 1–60 wt. % of a mesomorphic compound of the formula (I).

10. A liquid crystal composition according to claim 1, which comprises 1–40 wt. % of a mesomorphic compound of the formula (I).

11. A composition according to claim 1, which comprises a mesomorphic compound of the formula (I) represented by the following formula:

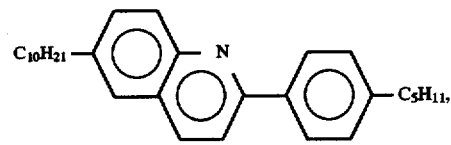

a mesomorphic compound of the formula (I) represented by the following structural formula:

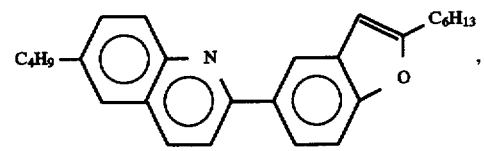

and a mesomorphic compound of the formula (I) represented by the following structural formula:

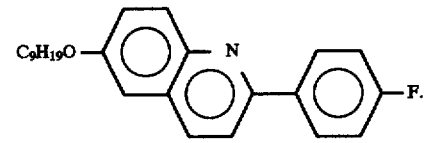

12. A composition according to claim 1, which comprises a mesomorphic compound of the formula (I) represented by the following formula:

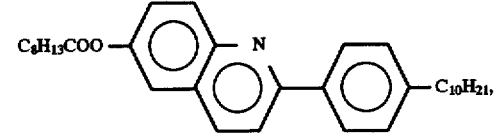

a mesomorphic compound of the formula (I) represented by the following structural formula:

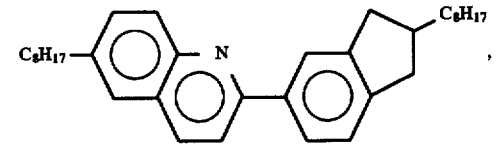

and a mesomorphic compound of the formula (I) represented by the following structural formula:

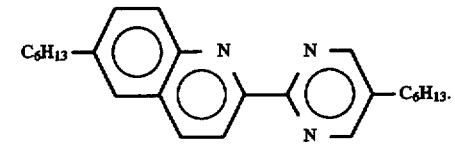

13. A composition according to claim 1, which comprises a mesomorphic compound of the formula (I) represented by the following formula:

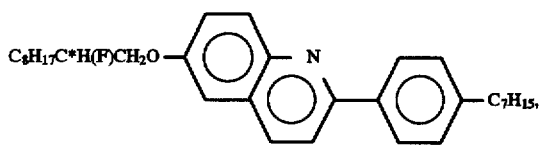

a mesomorphic compound of the formula (I) represented by the following structural formula:

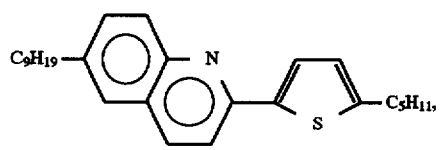

and a mesomorphic compound of the formula (I) represented by the following structural formula:

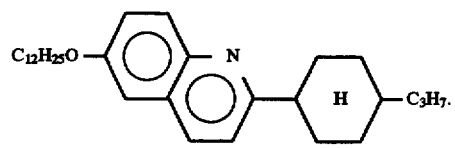

14. A composition according to claim 1, which comprises a mesomorphic compound of the formula (I) represented by the following formula:

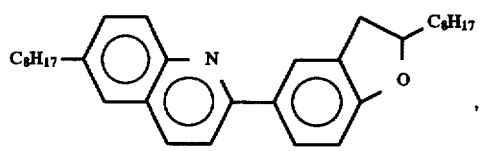

a mesomorphic compound of the formula (I) represented by the following structural formula:

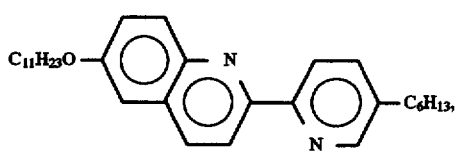

and a mesomorphic compound of the formula (I) represented by the following structural formula:

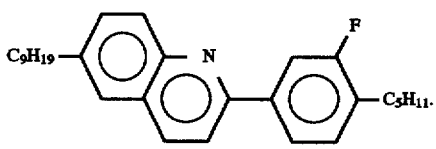

15. A composition according to claim 1, which comprises a mesomorphic compound of the formula (I) represented by the following formula:

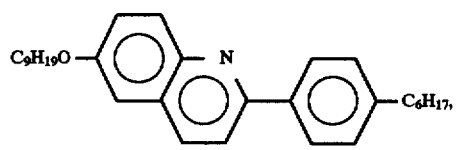

a mesomorphic compound of the formula (I) represented by the following structural formula:

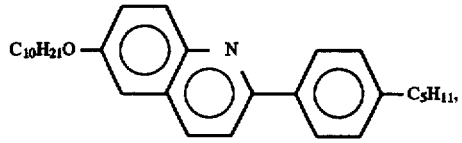

and a mesomorphic compound of the formula (I) represented by the following structural formula:

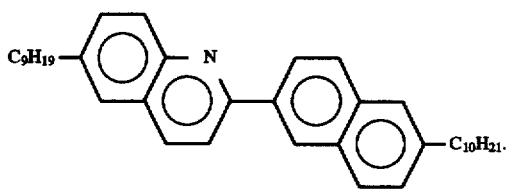

16. A composition according to claim 1, which comprises a mesomorphic compound of the formula (I) represented by the following formula:

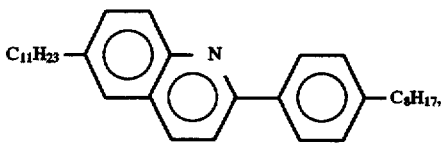

a mesomorphic compound of the formula (I) represented by the following structural formula:

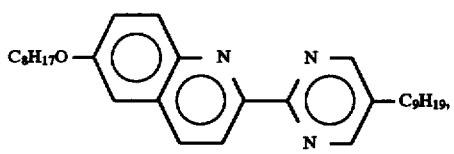

and a mesomorphic compound of the formula (I) represented by the following structural formula:

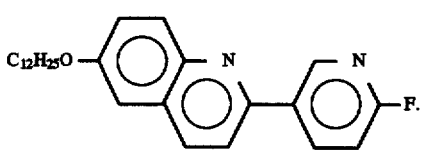

17. A liquid crystal device, comprising a pair of electrode plates and a liquid crystal composition according to any one of claims 1, 8, 9, 10, 11, 12, 13, 14, 15 and 16 disposed between the electrode plates.

18. A device according to claim 17, which further comprises an alignment control layer.

19. A device according to claim 18, wherein the alignment control layer has been subjected to uniaxial alignment treatment.

20. A device according to claim 17, wherein the liquid crystal composition is disposed in a thickness suppressing formation of a helical structure of liquid crystal molecules between the electrode plates.

21. A liquid crystal apparatus comprising a liquid crystal device according to claim 17.

22. An apparatus according to claim 21, wherein the liquid crystal device is a display device.

23. An apparatus according to claim 22, which further comprises a drive circuit for the liquid crystal device.

24. An apparatus according to claim 22, which further comprises a light source.

25. A display method, comprising:

providing a liquid crystal composition according to claim 1; and controlling the alignment direction of liquid crystal molecules in accordance with image data to effect display.

* * * * *

UNITED STATES PATENT AND TRADEMARK OFFICE
CERTIFICATE OF CORRECTION

PATENT NO. : 5,695,684
DATED : December 9, 1997
INVENTOR(S) : YOKO KOSAKA ET AL.

It is certified that error appears in the above-identified patent and that said Letters Patent is hereby corrected as shown below:

Title page, item [56], References Cited, U.S. PATENT DOCUMENTS:

Insert:

| | | |
|---|---|---|
| 4,367,924 | 1/1983 | Clark et al. |
| 5,091,109 | 2/1992 | Takiguchi et al. |
| 5,190,690 | 3/1993 | Takiguchi et al. |
| 5,217,644 | 6/1993 | Nohira et al. |
| 5,236,619 | 8/1993 | Iwaki et al. |
| 5,284,599 | 2/1994 | Iwaki et al. |
| 5,385,692 | 1/1995 | Iwaki et al. |
| 3,164,599 | 1/1965 | Rapoport |
| 4,402,849 | 9/1983 | Krause et al. |

Title page, item [56], References Cited, FOREIGN PATENT DOCUMENTS:

Insert:

| | | |
|---|---|---|
| 56-107216 | 8/1981 | Japan |
| 04-272989 | 9/1992 | Japan |
| 04-316555 | 11/1992 | Japan |
| 04-368370 | 12/1992 | Japan |

UNITED STATES PATENT AND TRADEMARK OFFICE
CERTIFICATE OF CORRECTION

PATENT NO. : 5,695,684
DATED : December 9, 1997
INVENTOR(S) : YOKO KOSAKA ET AL.

It is certified that error appears in the above-identified patent and that said Letters Patent is hereby corrected as shown below:

Title page, item [56], REFERENCES CITED, OTHER PUBLICATIONS:
Insert:
  M. Schadt and W. Helfrich, "Voltage-dependent optical activity of a twisted nematic liquid crystal", Appl. Phys. Lett. 18 (14), 2/15/71, pp. 127-8.

COLUMN 5:
  Line 13, "either" should read --ether--;
  Line 47, "acympanying" should read --accompanying--.

COLUMN 7:
  Line 11, "denotes" should read --denote-- (both occurances).

COLUMN 8:
  Reaction Scheme, "(DCCC)" should read --(DCC)--.

COLUMN 11:
  Line 48, "is an integer" should read --are integers--.

UNITED STATES PATENT AND TRADEMARK OFFICE
CERTIFICATE OF CORRECTION

PATENT NO. : 5,695,684
DATED : December 9, 1997
INVENTOR(S) : YOKO KOSAKA ET AL.

Page 3 of 5

It is certified that error appears in the above-identified patent and that said Letters Patent is hereby corrected as shown below:

COLUMN 12:
  Line 36, "$C_{11}H_{23}O-$" should read --$C_{11}H_{23}O$---;
  Line 45, "-EP-" should read ---Ep---;
  Line 46, "-EP-" should read ---Ep---.

COLUMN 14:
  Line 51, ""$R_7'-(PhY_7')Q$" should read --$R_7'-(PhY_7')_Q$--.

COLUMN 16:
  Line 4, "and" should be deleted.

COLUMN 17:
  Line 55, "with," should read --with--.

COLUMN 21:
  Example 3, "$C_6H_{17}-$" should read --$C_8H_{17}$---;
  Line 58, "second" should read --seconds--.

UNITED STATES PATENT AND TRADEMARK OFFICE
CERTIFICATE OF CORRECTION

PATENT NO. : 5,695,684
DATED : December 9, 1997
INVENTOR(S) : YOKO KOSAKA ET AL.

It is certified that error appears in the above-identified patent and that said Letters Patent is hereby corrected as shown below:

COLUMN 23:
  Line 23, "$C_9H_{19}$" should read --$C_9H_{19}O$--.

COLUMN 24:
  Exhibition Comparative Number I-35, "$C_8H_{17}$-Q-Ph-Cm-$C_8H_{17}$" should read --$C_8H_{17}$-Q-Cm-$C_8H_{17}$--.

COLUMN 25:
  Line 2, "devices" should read --device--;
  Line 3, "were" should read --was--;
  Line 43, "an" should be deleted;
  Exhibition Comparative Number I-63, "-NP-" should read ---Np--.

COLUMN 26:
  Line 35, "Crystal" should read --crystal--.

UNITED STATES PATENT AND TRADEMARK OFFICE
CERTIFICATE OF CORRECTION

PATENT NO. : 5,695,684

DATED : December 9, 1997

INVENTOR(S) : YOKO KOSAKA ET AL.

It is certified that error appears in the above-identified patent and that said Letters Patent is hereby corrected as shown below:

<u>COLUMN 29</u>:
  Line 5, "solution" should read --solution of--;
  Line 6, delete "i2 ml of";

Line 19, " $\underset{111}{\overset{110}{\rightleftarrows}}$ " should read -- $\underset{110}{\overset{110}{\rightleftarrows}}$ --.

<u>COLUMN 31</u>:
  Line 15, "(2)$C_bH_{2b}$" should read (2)$C_bH_{2b+1}$--.

Signed and Sealed this

Twenty-second Day of September, 1998

Attest:

BRUCE LEHMAN

Attesting Officer     Commissioner of Patents and Trademarks